US006555587B1

(12) United States Patent
Guire et al.

(10) Patent No.: US 6,555,587 B1
(45) Date of Patent: Apr. 29, 2003

(54) LATENT REACTIVE BLOOD COMPATIBLE AGENTS

(75) Inventors: Patrick E. Guire, Eden Prairie, MN (US); Aron B. Anderson, Minnetonka, MN (US); Richard A. Amos, St. Anthony, MN (US); Terrence P. Everson, Eagan, MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 10/207,944

(22) Filed: Jul. 29, 2002

Related U.S. Application Data

(62) Division of application No. 09/177,318, filed on Oct. 22, 1998, now Pat. No. 6,465,525.
(60) Provisional application No. 60/078,383, filed on Mar. 18, 1998.

(51) Int. Cl.[7] .................. A01N 35/00; A01N 37/00; A61K 31/74; A61M 25/00; A61F 2/06
(52) U.S. Cl. .................. 514/686; 514/687; 514/559; 514/558; 514/616; 514/621; 554/36; 554/37; 554/63; 424/78.08; 604/226; 623/1.11; 623/11.11
(58) Field of Search .................. 514/686, 687, 514/559, 558, 616, 621; 554/36, 37, 63; 424/78.08; 604/266; 623/1.11, 11.11

(56) References Cited

U.S. PATENT DOCUMENTS

| 3,992,356 A | 11/1976 | Jacquet et al. ............ 526/310 |
| 4,530,974 A | 7/1985 | Munro et al. ............ 525/329 |
| 4,722,906 A | 2/1988 | Guire ............ 436/501 |
| 4,973,493 A | 11/1990 | Guire ............ 427/2 |
| 4,979,959 A | 12/1990 | Guire ............ 623/66 |
| 5,002,582 A | 3/1991 | Guire et al. ............ 623/66 |
| 5,017,670 A | 5/1991 | Frautschi et al. ............ 527/313 |
| 5,073,171 A | 12/1991 | Eaton ............ 604/266 |
| 5,098,977 A | 3/1992 | Frautschi et al. ............ 527/313 |
| 5,217,492 A | 6/1993 | Guire et al. ............ 623/11 |
| 5,258,041 A | * 11/1993 | Guire et al. |
| 5,263,992 A | 11/1993 | Guire ............ 623/66 |
| 5,512,329 A | * 4/1996 | Guire et al. |

FOREIGN PATENT DOCUMENTS

| WO | WO 88/02623 | 4/1988 |
| WO | WO 89/05616 | 6/1989 |
| WO | WO 97/34935 | * 9/1993 |
| WO | WO 97/34935 | 9/1997 |
| WO | WO 99/16907 | 4/1999 |

OTHER PUBLICATIONS

Leonard, E.F., et al. *Ann. N.Y. Acad. Sci. 516*, New York, Acad. Sci., New York, 1987.
Sevastianov, V.I., *CRC Crit. Rev. Biocomp.* 4;109, 1988.
"Plastics", pp. 462–464, in *Concise Encyclopedia of Polymer Science and Engineering*, Kroschwitz, ed., John Wiley and Sons, 1990.

* cited by examiner

Primary Examiner—Thurman K. Page
Assistant Examiner—Isis Ghali
(74) Attorney, Agent, or Firm—Fredrikson & Byron, P.A.

(57) ABSTRACT

A reagent and related method for use in passivating a biomaterial surface, the reagent including a latent reactive group and a bifunctional aliphatic acid (e.g., fatty acid), in combination with a spacer group linking the latent reactive group to the aliphatic acid in a manner that preserves the desired function of each group. Once bound to the surface, via the latent reactive group, the reagent presents the aliphatic acid to the physiological environment, in vivo, in a manner (e.g., concentration and orientation) sufficient to hold and orient albumin.

10 Claims, No Drawings

LATENT REACTIVE BLOOD COMPATIBLE AGENTS

CROSS REFERENCE TO RELATED APPLICATIONS

The present application is a divisional of U.S. patent application filed Oct. 22, 1998 and assigned Ser. No. 09/177,318 now U.S. Pat. No. 6,465,525, which is a continuation of provisional U.S. patent application filed Mar. 18, 1998 and assigned Ser. No. 60/078,383, the entire disclosure of which is incorporated herein by reference.

TECHNICAL FIELD

The present invention relates to reagents and methods for rendering a surface biocompatible, and in particular to reagents and methods for "passivating" the surface of an implantable medical device in order to render it hemocompatible. In another aspect, the invention relates to biomedical devices, per se, and in particular those having biocompatible, including hemocompatible, tissue-contacting surfaces.

BACKGROUND OF THE INVENTION

Manufacturers of implantable medical devices have long attempted to understand, and in turn improve, the performance of materials used in blood-contacting applications (Leonard, E. F., et al. *Ann. N.Y. Acad. Sci.* 516, New York, Acad. Sci., New York, 1987). The biological response of the body, as well as problems with infection, have hindered the application of implantable, disposable, and extracorporeal devices. Anticoagulant drugs, such as heparin and coumadin, can improve the use of such devices, although anticoagulants have their own corresponding risks and drawbacks. For these reasons, development of materials having greater compatibility with blood has been pursued aggressively (Sevastianov, V. I., *CRC Crit. Rev. Biocomp.* 4:109, 1988).

Two general strategies that have been used to develop improved blood-contacting materials include modifying the chemistry of the bulk material itself, and/or modifying the interfacial properties of the material. With regard to the latter approach, several classes of materials have been covalently bonded onto blood-contacting surfaces with the goal of improving blood compatibility. These include anticoagulants, such as heparin and hirudin; hydrogels; polyethylene oxide (PEO); albumin binding agents; cell membrane components; prostaglandins; and sulfonated polymers. These approaches have met with varying degrees of success in terms of reducing protein adsorption, platelet adhesion and activation, and thrombus formation. Unfortunately, no approach has yet been shown to be universally applicable for improving blood-biomaterial interactions.

As mentioned above, albumin binding agents have been considered for use on biomaterials. Biomaterials having a high surface concentration of albumin have been shown to be less likely to initiate the fibrin cascade and platelet attachment than those having a high concentration of other serum proteins, such as fibrinogen, fibronectin, or immunoglobulins. On many polymeric materials, however, fibrinogen is often the predominant protein adsorbed from protein mixtures or plasma. For these reasons, investigators have attempted to immobilize albumin onto materials or to design biomaterial surfaces that will enhance binding of endogenous albumin from blood, thus mitigating the adsorption of fibrinogen and consequent thrombogenic phenomena.

In this respect, a number of different approaches have been employed to date. These approaches include passive adsorption or covalent immobilization of albumin to the surface, and the development of surfaces designed to selectively bind endogenous albumin from circulating blood, the latter using alkyl chain-modified materials and other means.

Munro, et al., U.S. Pat. No. 4,530,974, discloses a method of adsorbing albumin to a water-insoluble polymer such as polyurethane by covalently binding to the surface a nonionic hydrophobic aliphatic chain to which serum albumin will selectively bind.

Frautschi et al., U.S. Pat. Nos. 5,017,670 and 5,098,977, teach methods for covalent attachment of aliphatic extensions of 12 to 22 carbon atoms to water-insoluble polymers containing aromatic rings and ring structures with adjacent secondary hydroxyls for increased albumin binding.

Eaton, U.S. Pat. No. 5,073,171, describes a biocompatible prosthetic device incorporating an amount of an albumin binding dye effective to form a coating of endogeneous albumin on the device when the device is in contact with a physiological fluid containing albumin.

While some or all of these various strategies can be used to enhance the binding of endogenous albumin to blood-contacting material surfaces, and in turn to reduce fibrinogen binding, these approaches are each limited in one or more respects. Alkyl chain-modified surfaces have been shown to increase albumin binding and decrease fibrinogen binding, but these effects were fairly limited, for instance, to a short term time frame (generally less than one hour). In addition, various other surface modification methods discussed above are useful for only a narrow range of substrate materials.

On another subject, the assignee of this application has developed the ability to attach bioactive groups to a surface by covalently bonding those groups, directly or indirectly, to the surface. For instance, U.S. Pat. Nos. 4,722,906, 4,979, 959, 4,973,493 and 5,263,992 relate to devices having biocompatible agents covalently bound via photoreactive groups and a chemical linking moiety to the biomaterial surface. U.S. Pat. Nos. 5,258,041 and 5,217,492 relate to the attachment of biomolecules to a surface through the use of long chain chemical spacers. U.S. Pat. Nos. 5,002,582 and 5,512,329 relate to the preparation and use of polymeric surfaces, wherein polymeric agents providing desirable properties are covalently bound via a photoreactive moiety to the surface. In particular, the polymers themselves exhibit the desired characteristics, and in the preferred embodiment, are substantially free of other (e.g., bioactive) groups.

It would be highly desirable to be able to attach albumin to a biomaterial surface in a manner that is suitably stable for extended use, particularly in a manner that permits the albumin to be replenished over time and in the course of use.

SUMMARY OF THE INVENTION

The present invention provides a novel reagent for use in passivating a biomaterial surface, the reagent comprising a latent reactive group and a bifunctional aliphatic acid, in combination with a spacer group linking the latent reactive group to the aliphatic acid in a manner that preserves the desired function of each group. The reagent can be used to passivate a surface by activating the latent reactive group in the presence of the surface in order to covalently bond the reagent to the surface. Once bound to the surface, the reagent presents the aliphatic acid to the physiological environment, in vivo, in a manner (e.g., concentration and orientation) sufficient to hold and orient albumin. Preferably, over time, the reagent surface is able to replenish itself by replacing albumin molecules that have become unbound or deteriorated with new albumin molecules. Albumin (e.g., human serum albumin (HSA)), is defined as any naturally occurring proteinaceous moiety containing a fatty acid binding site.

In a preferred embodiment, the reagent is of the general formula $(X)_m$—Y—$(Z)_n$ where X is a latent reactive (e.g., photoreactive) group, Y is a spacer radical, and Z is a bifunctional aliphatic acid, as each are described herein. The values of m and n are $\geq 1$ and while m can equal n, it is not necessary. The aliphatic acid is 'bifunctional' in that it provides both an aliphatic region and an anionic (e.g., carboxylic acid) region. Once attached to a surface, these portions cooperate in the process of attracting and binding of albumin in order to passivate the surface.

In the preferred embodiment where both m and n=1, the reagent is termed a heterobifunctional reagent. The aliphatic acid is preferably attached to the latent reactive group by means of a divalent spacer group in a manner that does not detrimentally affect the function of either the aliphatic or anionic portions. Higher-valent spacer groups can also be selected which permit the attachment of multiple aliphatic acid and latent reactive groups, again in a manner which does not detrimentally affect the functions of the respective groups. In this case m does not necessarily equal n and both are $\geq 1$.

In a further embodiment, the spacer group can be a multivalent polymer having multiple sites along the backbone which permit covalent attachment of the aliphatic acid and latent reactive groups. These groups can be attached to a preformed reactive polymer using conventional chemical coupling techniques or may be incorporated during the polymerization process by use of appropriately substituted monomers. In this embodiment, m does not necessarily equal n and typically both are larger than one.

The invention further provides a method for preparing a passivating reagent, as well as a method of using the reagent to passivate the surface of a synthetic or natural biomaterial. In yet a further embodiment, the invention provides a surface coated with a passivating reagent of this invention, and in turn, an article fabricated from a material providing a surface coated or coatable with such a reagent. In yet a further embodiment, the invention provides a passivated biomaterial surface having reagent attached thereto and albumin attracted and attached to the bound reagent.

DETAILED DESCRIPTION

The present invention permits the binding of albumin to a surface to be enhanced by the use of a surface modification reagent. The reagent includes a bifunctional aliphatic acid capable of being attached to a surface in an amount and orientation that improves the ability of the surface to attract and bind albumin. While not intending to be bound by theory, it appears that a surface bearing a reagent of this invention exhibits improved albumin binding by virtue of both hydrophobic interactions (of the alkyl chain) and ionic interactions (of the anionic moiety) with albumin. It is expected that the hydrophobic interactions serve to hold and orient the free albumin molecule, while the ionic interactions serve to maintain the albumin molecule in position by the addition of attractive ionic forces. In a particularly preferred embodiment, the bifunctional aliphatic acid is attached to either alkane, oxyalkane, or hydrophobic polymeric backbones to allow both aliphatic and ionic regions of the bifunctional acid analog to spacially orient away from the biomaterial surface to induce better binding with native albumin. The reagent, in turn, permits albumin binding surfaces to be created using a variety of medical device materials, and in particular, for use in blood-contacting medical devices.

Bifunctional Aliphatic Acid

The bifunctional aliphatic acid of the present invention ("Z" group) includes both an aliphatic portion and an anionic portion. The word "aliphatic", as used herein, refers to a substantially linear portion, e.g., a hydrocarbon backbone, capable of forming hydrophobic interactions with albumin. The word "anionic", in turn, refers to a charged portion capable of forming further ionic interactions with the albumin molecule. By the use of a reagent of this invention, these portions can be covalently attached to a surface in a manner that retains their desired function, in order to attract and bind native albumin from blood and other bodily fluids.

In a preferred embodiment, the invention includes photoactivatible molecules having fatty acid functional groups, including polymers having multiple photoactivatible and fatty acid functional groups, as well as heterobifunctional molecules. Photoactivatible polyacrylamide copolymers containing multiple pendant fatty acid analogs and multiple pendant photogroups have been synthesized from acrylamide, a benzophenone-substituted acrylamide, and N-substituted acrylamide monomers containing the fatty acid analog. Photoactivatible polyvinylpyrrolidones have also been prepared in a similar fashion. Polyacrylamide or polyvinylpyrrolidone copolymers with a single end-point photogroup and multiple pendant fatty acid analogs have also been synthesized. Finally, photoactivatible, heterobifunctional molecules having a benzophenone on one end and a fatty acid group on the other end optionally separated by a spacer have been made, wherein that spacer can be a hydrophobic alkyl chain or a more hydrophilic polyethyleneglycol (PEG) chain.

Spacer Group

Suitable spacers ("Y" groups) for use in preparing heterobifunctional reagents of the present invention include any di- or higher-functional spacers capable of covalently attaching a latent reactive group to an aliphatic acid in a manner that permits them both to be used for their intended purpose. Although the spacer may itself provide a desired chemical and/or physical function, preferably the spacer is non-interfering, in that it does not detrimentally affect the use of the aliphatic and ionic portions for their intended purposes. In the case of the polymeric reagents of the invention, the spacer group serves to attach the aliphatic acid to the backbone of the polymer.

The spacer may be either aliphatic or polymeric and contain various heteroatoms such as O, N, and S in place of carbon. Constituent atoms of the spacers need not be aligned linearly. For example, aromatic rings, which lack abstractable hydrogen atoms (as defined below), can be included as part of the spacer design in those reagents where the latent reactive group functions by initiating covalent bond formation via hydrogen atom abstraction. In its precursor form (i.e., prior to attachment of a photoreactive group and aliphatic acid), a spacer can be terminated with any suitable functionalities, such as hydroxyl, amino, carboxyl, and sulfhydryl groups, which are suitable for use in attaching a photoreactive group and the aliphatic acid by a suitable chemical reaction, e.g., conventional coupling chemistry.

Alternatively, the spacer can be formed in the course of combining a precursor containing (or capable of attaching) the photoreactive group with another containing (or capable of attaching) the aliphatic acid. For example, the aliphatic acid could be reacted with an aliphatic diamine to give an aliphatic amine derivative of the bifunctional aliphatic acid and which could be coupled with a carboxylic acid containing the photogroup. To those skilled in the art, it would be obvious that the photogroup could be attached to any appropriate thermochemical group which would react with any appropriate nucleophile containing O, N or S.

Examples of suitable spacer groups include, but are not limited to, the groups consisting of substituted or unsubstituted alkylene, oxyalkylene, cycloalkylene, arylene, oxyarylene, or aralkylene group, and having amides, ethers, and carbonates as linking functional groups to the photoactivatible group, and the bifunctional aliphatic fatty acid.

The spacer of the invention can also comprise a polymer which serves as a backbone. The polymer backbone can be either synthetic or naturally occurring, and is preferably a synthetic polymer selected from the group consisting of oligomers, homopolymers, and copolymers resulting from addition or condensation polymerization. Naturally occurring polymers, such as polysaccharides, can be used as well. Preferred backbones are biologically inert, in that they do not provide a biological function that is inconsistent with, or detrimental to, their use in the manner described.

Such polymer backbones can include acrylics such as those polymerized from hydroxyethyl acrylate, hydroxyethyl methacrylate, glyceryl acrylate, glyceryl methacrylate, acrylic acid, methacrylic acid, acrylamide and methacrylamide; vinyls such as polyvinylpyrrolidone and polyvinyl alcohol; nylons such as polycaprolactam; derivatives of polylauryl lactam, polyhexamethylene adipamide and polyhexamethylene dodecanediamide, and polyurethanes; polyethers such as polyethylene oxide, polypropylene oxide, and polybutylene oxide; and biodegradable polymers such as polylactic acid, polyglycolic acid, polydioxanone, polyanhydrides, and polyorthoesters.

The polymeric backbone is chosen to provide a backbone capable of bearing one or more photoreactive groups, and one or more fatty acid functional groups. The polymeric backbone is also selected to provide a spacer between the surface and the various photoreactive groups and fatty acid functional groups. In this manner, the reagent can be bonded to a surface or to an adjacent reagent molecule, to provide the fatty acid functional groups with sufficient freedom of movement to demonstrate optimal activity. The polymer backbones are preferably water soluble, with polyacrylamide and polyvinylpyrrolidone being particularly preferred polymers.

Photoreactive Group

In a preferred embodiment one or more photoreactive groups are provided by the X groups attached to the central Y spacer radical. Upon exposure to a suitable light source, each of the photoreactive groups are subject to activation. The term "photoreactive group", as used herein, refers to a chemical group that responds to an applied external energy source in order to undergo active specie generation, resulting in covalent bonding to an adjacent chemical structure (e.g., an aliphatic carbon-hydrogen bond).

Preferred X groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones are preferred, such as acetophenone, benzophenone, anthraquinone, anthrone, and anthrone-like heterocycles (i.e., heterocyclic analogues of anthrone such as those having N, O, or S in the 10- position), or their substituted (e.g., ring substituted) derivatives. The functional groups of such ketones are preferred since they are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (for example, from a support surface or target molecule in the solution and in bonding proximity to the agent), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are particularly preferred.

The azides constitute a preferred class of latent reactive groups and include arylazides ($C_6R_5N_3$) such as phenyl azide and particularly 4-fluoro-3-nitrophenyl azide, acyl azides (—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive groups and include diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—CO—$CN_2$—CO—O—) such as t-butyl alpha diazoacetoacetate. Other photoreactive groups include aliphatic azo compounds such as azobisisobutyronitrile, diazirines (—$CHN_2$) such as 3-trifluoromethyl-3-phenyldiazirine and ketenes (—CH=C=O) such as ketene and diphenylketene.

Upon activation of the photoreactive groups, the coating adhesion molecules are covalently bound to each other and/or to the material surface by covalent bonds through residues of the photoreactive groups. Exemplary photoreactive groups, and their residues upon activation, are shown as follows.

| Photoreactive Group | Residue Functionality | |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2PO$—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

Preparation of Reagents

Reagents of the present invention can be prepared by any suitable means, depending upon the selection of either a heterobifunctional reagent or a polymeric reagent. In the case of the heterobifunctional reagents, the fatty acid residue is provided by a fatty acid possessing a chemically reactive group on the alkyl chain which permits covalent coupling of the remainder of the heterobifunctional molecule to the fatty acid with preservation of the carboxylic acid functionality. Preferably, the site of the reactive group is in close proximity to the carboxylic acid group so as to minimize effects on the binding activity of the hydrophobic alkyl chain. Most preferably, the fatty acid residue can be provided by a compound such n-tetradecylsuccinic anhydride (TDSA). Reaction of such a molecule with a second molecule possessing a nucleophilic species such as a primary amine results in opening of the anhydride ring to give a fatty acid with an amide linkage to the remainder of the molecule. This reaction generates a pair of regioisomers depending upon the direction of the anhydride ring opening. The second molecule in this reaction can be provided by a spacer group, with or without a photoactivatible group, which possesses a group capable of reaction with the fatty acid compound. Most preferably, this spacer group possesses an amine which is highly reactive with an anhydride species. The spacer group is typically a bifunctional molecule which can have the photoactivatible group attached prior to reaction with the fatty acid derivative or the reverse order of reaction can be used. The bifunctional spacer can be either heterobifunctional or homobifunctional, with the former requiring a differential reactivity in the first and second reaction steps and the latter requiring an efficient method of separating the monofunctionalized spacer following the first reaction. Optionally, no spacer is required and a photoactivatible group possessing functionality capable of reaction with the fatty acid derivative can be used. The above examples are nonlimiting and the methods of accomplishing these coupling reactions are apparent to those skilled in the art.

Polymeric reagents of the invention can be prepared by derivatization of preformed polymers possessing reactive groups along the backbone of the polymer capable of reaction with the photoactivatible groups and the fatty acid derivatives. For example, polyacrylamide, polyvinylpyrrolidone, or siloxanes functionalized with amine groups along the backbone, with or without a spacer group, can be reacted with 4-benzoylbenzoyl chloride (BBA-Cl) and TDSA to provide the photoactivatible and fatty acid ligands respectively. Alternatively, the photoactivatible and fatty acid groups can be prepared in the form of polymerizable monomers which can then be copolymerized with themselves and other monomers to provide polymers of the invention. In a further embodiment of the invention, the photoactivatible group can be introduced in the form of a chain transfer agent along with the fatty acid monomer and other comonomers so as to provide a polymer having the photoactivatible group at the end of the polymer chain. For example, a chain transfer agent possessing two derivatized benzophenones as the photoactivatible groups and a mercaptan as the chain transfer agent can be used to copolymerize a fatty acid monomer and acrylamide or N-vinylpyrrolidone monomers to provide polymers of the invention. Alternatively, this polymer could be prepared with reactive groups along the backbone, followed by reaction with a fatty acid derivative.

Surfaces and Methods of Attachment.

The reagent of the present invention can be used to modify any suitable surface. Where the latent reactive group is a photoreactive group of the preferred type, it is particularly preferred that the surface provide abstractable hydrogen atoms suitable for covalent bonding with the activated group.

Plastics such as polyolefins, polystyrenes, poly(methyl) methacrylates, polyacrylonitriles, poly(vinylacetates), poly (vinyl alcohols), chlorine-containing polymers such as poly (vinyl) chloride, polyoxymethylenes, polycarbonates, polyamides, polyimides, polyurethanes, phenolics, aminoepoxy resins, polyesters, silicones, cellulose-based plastics, and rubber-like plastics can all be used as supports, providing surfaces that can be modified as described herein. See generally, "Plastics", pp. 462–464, in *Concise Encyclopedia of Polymer Science and Engineering,* Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Any suitable technique can be used for reagent binding to a surface, and such techniques can be selected and optimized for each material, process, or device. The reagent can be successfully applied to clean material surfaces as listed above by spray, dip, or brush coating of a solution of the fatty acid binding reagent. The surface may be air-dried prior to illumination or the surface can be illuminated while submerged in the coating solution. The photoreactive group is energized via an external stimulation (e.g., exposure to a suitable light source) to form, via free active specie generation, a covalent bond between the reagent and either another polybifunctional reagent molecule or the biomaterial surface. This coating method is herein termed the "one step coating method", since photoreactive coupling chemistry attaches an invention polymer to a biomaterial surface, and no subsequent steps are required to add the bioactive group. The external stimulation that is employed desirably is electromagnetic radiation, and preferably is radiation in the ultraviolet, visible or infrared regions of the electromagnetic spectrum.

The "two-step" method would involve a first step of photocoupling a hydrocarbon backbone to the surface, followed by a second step of attaching (e.g., thermochemically) one or more fatty acid derivatives to the immobilized backbone. For example, this two step approach could involve covalently attaching a photoreactive hydrocarbon backbone containing nucleophiles which could be used to thermochemically couple fatty acid derivatives to the surface, or directly attaching thermochemical groups (e.g. amines) to the surface, followed by thermochemical attachment of one or more fatty acid derivatives.

Alternatively, chemically reactive groups can be introduced on the surface by a variety of non-photochemical methods, followed by chemical coupling of the fatty acid group to the modified surface. For example, amine groups can be introduced on a surface by plasma treatment with a mixture of methane and ammonia and the resulting amines can then be reached with TDSA to chemically couple the fatty acid derivative to the surface through an amide linkage. When desired, other approaches can be used for surface modification using the reagent of the present invention. This approach is particularly useful in those situations in which a support is difficult to modify using conventional chemistry, or for situations that require exceptional durability and stability of the target molecule on the surface.

EXAMPLES

The invention will be further described with reference to the following non-limiting Examples, which incorporate the following table of formulas. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

| Formula | Compound/Example | Notation |
|---|---|---|
|  | 1/1 | 4-Benzoylbenzoyl chloride |
|  | 2/2 | 4-Bromomethyl-benzophenone |
|  | 3/3 | Poly(ethylene glycol)$_{200}$ Mono-4-benzoylbenzyl Ether |
| 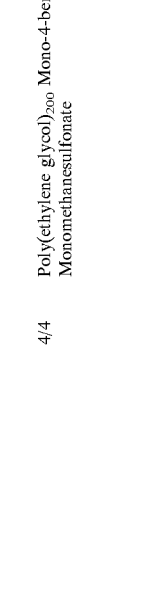 | 4/4 | Poly(ethylene glycol)$_{200}$ Mono-4-benzoylbenzyl Ether Monomethanesulfonate |
| 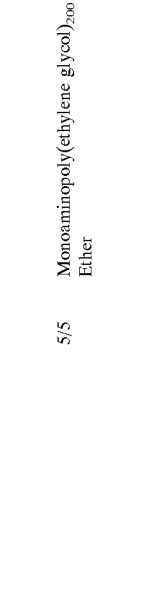 | 5/5 | Monoaminopoly(ethylene glycol)$_{200}$ Mono-4-benzoylbenzyl Ether |

-continued

| Compound/Example | Notation | Formula |
|---|---|---|
| 6/6 | Mono-2-(carboxymethyl)hexadecanamidopoly(ethylene glycol)$_{200}$ Mono-4-benzoylbenzyl Ether | Benzoylbenzyl-CH$_2$—(OCH$_2$CH$_2$)$_x$—NH—C(=O)—CH(CH$_2$OH)(CH$_2$)$_{13}$CH$_3$ with CO$_2$H |
| 7/6 | Mono-3-carboxyheptadecanamidopoly (ethylene glycol)$_{200}$ Mono-4-benzoylbenzyl Ether | Benzoylbenzyl-CH$_2$—(OCH$_2$CH$_2$)$_x$—NH—C(=O)—CH$_2$—CH((CH$_2$)$_{13}$CH$_3$)—CO$_2$H |
| 8/7 | Mono-2-(carboxymethyl)hexadecanamidotetra(ethylene glycol) Mono-4-benzoylbenzyl Ether | Benzoylbenzyl-CH$_2$—(OCH$_2$CH$_2$)$_4$—NH—C(=O)—CH(CH$_2$OH)(CH$_2$)$_{13}$CH$_3$ with CO$_2$H |
| 9/7 | Mono-3-carboxyhepta-decanamidotetra(ethylene glycol) Mono-4-benzoylbenzyl Ether | Benzoylbenzyl-CH$_2$—(OCH$_2$CH$_2$)$_4$—NH—C(=O)—CH$_2$—CH((CH$_2$)$_{13}$CH$_3$)—CO$_2$H |
| 10/8 | N-[2-(4-Benzoylbenzyloxy)ethyl]-2-(carboxymethyl) hexadecanamide | Benzoylbenzyl-CH$_2$O—CH$_2$CH$_2$—NH—C(=O)—CH(CH$_2$OH)(CH$_2$)$_{13}$CH$_3$ with CO$_2$H |

-continued

| Compound/Example | Notation |
|---|---|
| 11/8 | N-[2-(4-Benzoylbenzyloxy)ethyl]-3-(carboxyhepta-decanamide |
| 12/9 | N-[12-(Benzoylbenzyloxy)dodecyl]-2-(carboxymethyl)hexadecanamide |
| 13/9 | N-[12-(Benzoylbenzyloxy)dodecyl]-3-carboxy-heptadecanamide |
| 14/10 | N-[3-(4-Benzoylbenzamido)propyl]-2-(carboxymethyl)hexadecanamide |
| 15/10 | N-[3-4-Benzoylbenzamido)propyl]-3-carboxyhepta-decanamide |

-continued

| Compound/Example | Notation | Formula |
|---|---|---|
| 16/11 | N-(3-Benzoylphenyl)-2-(carboxymethyl)hexadecanamide | |
| 17/11 | N-(3-Benzoylphenyl)-3carboxyhepta-decanamide | |
| 18/12 | N-(4-Benzoylphenyl)-2-(carboxymethyl)hexadecanamide | |
| 19/12 | N-(4-Benzoylphenyl)-3-(carboxyhepta-decanamide | |
| 20/13 | Monohexadecanamidopoly(ethylene glycol)$_{200}$ Mono-4-benzoylbenzyl Ether | |

-continued

| Formula | Compound/Example | Notation |
|---|---|---|
| benzoyl-C6H4-CH2—(OCH2CH2)x̄—NH—C(=O)—CH2CH2CO2H | 21/14 | Mono-3-Carboxypropanamidopoly(ethylene glycol)$_{200}$ Mono-4-benzoylbenzyl Ether |
| benzoyl-C6H4-CH2O—(CH2)15CH3 | 22/15 | Hexadecyl 4-benzoylbenzil ether |
| benzoyl-C6H4-CH2—(OCH2CH2)x̄—O(CH2)15CH3 | 23/16 | Poly(ethylene glycol)$_{200}$ Monohexadecyl Mono-4-benzoylbenzyl Ether |
| benzoyl-C6H4-CH2—(OCH2CH2)x̄—O(CH2)15CO2H | 24/17 | Poly(ethylene glycol)$_{200}$ Mono-15-carboxypentadecyl Mono-4-benzoylbenzyl Ether |
| benzoyl-C6H4-CH2—(OCH2CH2)x̄—NH—C(=O)—(CH2)14CO2H | 25/18 | Mono-15-carboxypenta-decanamidopoly(ethylene glycol)$_{200}$ Mono-4-benzoylbenzyl Ether |
| CH2=C(CH3)—C(=O)—NH—(CH2)3—NH—C(=O)—CH[(CH2)13CH3]—CH2—CO2H | 26/19 | N-[3-Methacrylamido)propyl]-2-(carboxymethyl)hexadecanamide |

-continued

| Compound/Example | Notation | Formula |
|---|---|---|
| 27/19 | N-[3-Methacrylamido)propyl]-3-carboxyhepta-decanamide | |
| 28/20 | N-[3-(4-Benzoylbenzamido)propyl]methacrylamide | |
| 29/21 | N-(2-Mercaptoethyl)-3,5-bis(4-benzoylbenzyloxy)benzamide | |

| Compound/Example | Notation | Formula |
|---|---|---|
| 30/22 | Photoreactive Endpoint Copolymer of Acrylamide and Fatty Acid Monomers | 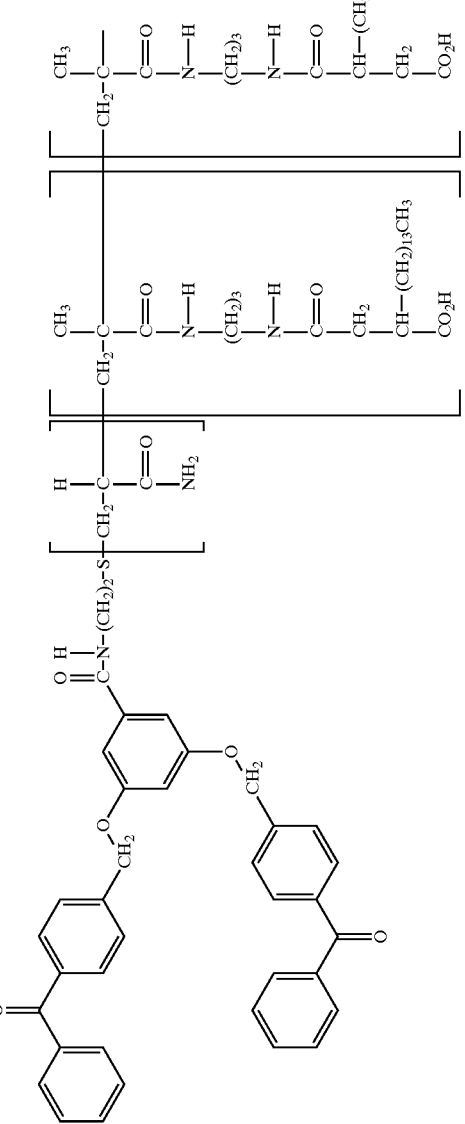 |
| 31/23 | Photoreactive Random Copolymer of Acrylamide and Fatty Acid Monomers | 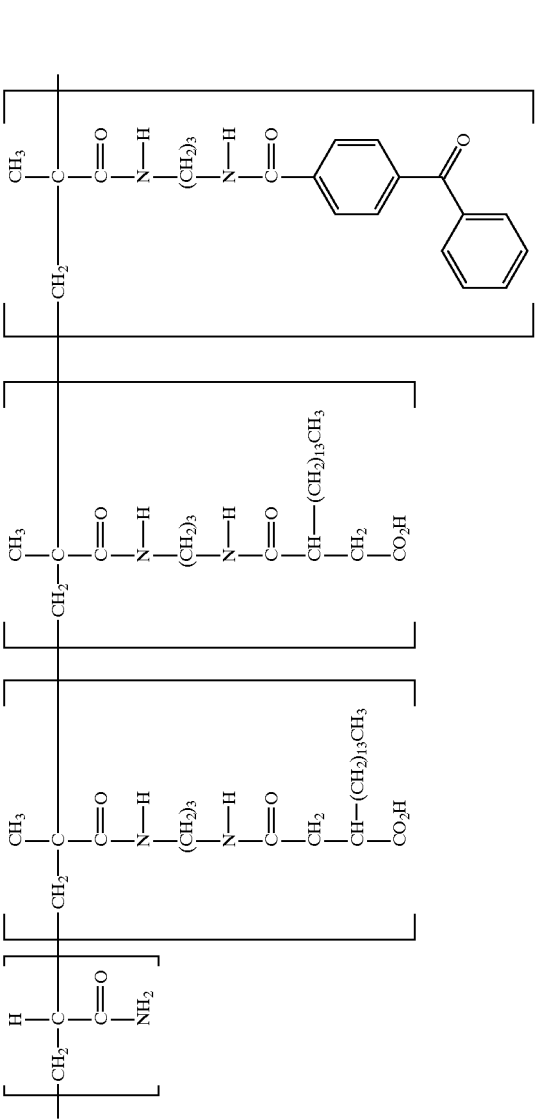 |

| Formula | Compound/Example | Notation |
|---|---|---|
| | 32A-C/24 | Photoreactive Endpoint Copolymer of N-Vinylpyrrolidone and Fatty Acid Monomers |

-continued

| Compound/Example | Notation | Formula |
|---|---|---|
| 33A–D/25 | Photoreactive Random Copolymer of N-Vinylpyrrolidone and Fatty Acid Monomers | (structure shown) |
| 34/26 | Photoreactive Siloxane Copolymer Containing Fatty Acid Ligands | (structure shown) |

Example 1

Preparation of 4-Benzoylbenzoyl Chloride (BBA-Cl) (Compound 1)

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide (DMF), 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from toluene/hexane (1/4) to give 988 g (91% yield) after drying in a vacuum oven. Product melting point was 92–94° C. Nuclear magnetic resonance (NMR) analysis at 80 MHz was consistent with the desired product. The final compound was stored for use in the preparation of photoactivatable compounds, as described for instance in Examples 10 and 20.

Example 2

Preparation of 4-Bromomethylbenzophenone (BMBP) (Compound 2)

4-Methylbenzophenone, 750 g (3.82 moles), was added to a 5 liter Morton flask equipped with an overhead stirrer and dissolved in 2850 ml of benzene. The solution was then heated to reflux, followed by the dropwise addition of 610 g (3.82 moles) of bromine in 330 ml of benzene. The addition rate was approximately 1.5 ml/min and the flask was illuminated with a 90 watt (90 joule/sec) halogen spotlight to initiate the reaction. A timer was used with the lamp to provide a 10% duty cycle (on 5 seconds, off 40 seconds), followed in one hour by a 20% duty cycle (on 10 seconds, off 40 seconds). At the end of the addition, the product was analyzed by gas chromatography and was found to contain 71% of the desired 4-bromomethylbenzophenone, 8% of the dibromo product, and 20% unreacted 4-methylbenzophenone. After cooling, the reaction mixture was washed with 10 g of sodium bisulfite in 100 ml of water, followed by washing with 3×200 ml of water. The product was dried over sodium sulfate and recrystallized twice from toluene/hexane (1/3 by volume (v/v)). After drying under vacuum, 635 g of BMBP were isolated, providing a yield of 60% and having a melting point of 112–114° C. Analysis on an NMR spectrometer was consistent with the desired product. The final compound was stored for use in the preparation of photoactivatable compounds, as described for instance in Examples 3, 7, 8, 9, 15, and 21.

Example 3

Preparation of Poly(ethylene glycol)$_{200}$ Mono-4-benzoylbenzyl Ether (Compound 3)

The poly(ethylene glycol)200 (PEG), 72.72 g (0.363 mol), was azeotroped with 200 ml of toluene for two hours to remove moisture, followed by the removal of excess toluene under vacuum. The PEG residue was then dissolved in 400 ml of anhydrous tetrahydrofuran (THF) while stirring under argon at 4° C. Sodium hydride, 2.90 g of a 60% mixture in mineral oil (72.5 mmol), was added in portions and the mixture was stirred 1 hour at room temperature. BMBP, 20.0 g (72.7 mmol), prepared according to the general method described in Example 2, was added as a solution in 100 ml of THF over a 2 hour period and the mixture was stirred 16 hours at room temperature under argon. The reaction was quenched with aqueous ammonium chloride (36 g in 200 ml of water) and the organic solvent was removed under vacuum. The residue was dissolved in brine, extracted with chloroform, and the resulting organic extracts were dried over sodium sulfate. The product was isolated as a viscous oil by adding the chloroform solution to diethyl ether, resulting in precipitation of 27.64 g of the desired product. The product was used without additional purification. Analysis on an NMR spectrometer was consistent with the desired product.

Example 4

Preparation of Poly(ethylene glycol)$_{200}$ Mono-4-benzoylbenzyl Ether Monomethanesulfonate (Compound 4)

Compound 3, 3.0 g (7.61 mmol), prepared according to the general method described in Example 3, was dissolved in 25 ml of methylene chloride, followed by the addition of 1.5 g (14.8 mmol) of triethylamine (TEA). The mixture was cooled on an ice bath under argon and 1.3 g (11.3 mmol) of methanesulfonyl chloride (MsCl)were added dropwise over a 10 minute period. The reaction temperature was allowed to rise to ambient temperature overnight. The precipitated salts were removed by filtration and the solvent was removed under vacuum. The residue was dissolved in toluene and filtered to remove solids, followed by evaporation under vacuum to give 3.01 g of product. No further purification of the product was done at this point. Analysis on an NMR spectrometer was consistent with the desired product.

Example 5

Preparation of Monoaminopoly(ethylene glycol)$_{200}$ Mono-4-benzoylbenzyl Ether (Compound 5)

Compound 4, 17.97 g (38.07 mmol), prepared according to the general method described in Example 4, was dissolved in 100 ml of anhydrous THF in a thick-walled tube, followed by the addition of 100 ml of concentrated ammonium hydroxide. The tube was sealed and the two phase mixture was stirred vigorously at 65° C. for 16 hours. The solvent was removed under vacuum and the resulting residue was dissolved in chloroform. The product was loaded on a silica gel flash chromatography column and eluted with chloroform/acetone/acetic acid (60/40/1 v/v) until all of the less polar impurities were removed. The product was then eluted with chloroform/methanol/acetic acid/water (85/15/1/1 v/v). The fractions which were UV, ninhydrin, and Dragendorff positive were pooled and the solvent was removed under vacuum to give 8.63 g of product. Analysis on an NMR spectrometer was consistent with the desired product.

Example 6

Preparation of Mono-2-(carboxymethyl)hexadecanamidopoly(ethylene glycol)$_{200}$ Mono-4-benzoylbenzyl Ether (Compound 6) and Mono-3-carboxyheptadecanamidopoly(ethylene glycol)$_{200}$ Mono-4-benzoylbenzyl Ether (Compound 7)

Compound 5, 3.03 g (7.71 mmol), prepared according to the general method described in Example 5, and TEA, 2.24 g (22.1 mmol), were dissolved in 30 ml of methylene chloride, followed by the addition of 2.40 g (8.10 mmol) of TDSA as the solid. The reaction mixture was stirred 18 hours at room temperature under argon. The solvents were removed under vacuum and the resulting oil was purified by silica gel flash chromatography using a solvent gradient: 500 ml of ether/hexane (75/25 v/v); 500 ml of ether/hexane/acetic acid (75/25/1 v/v); chloroform/acetone/acetic acid (60/40/1 v/v); and chloroform/methanol/acetic acid/water (85/15/1/1 v/v). The fractions were pooled to give two separate UV and Dragendorff positive materials representing the regioisomers resulting from ring opening of the anhydride ring. Evaporation of solvent gave 1.35 g of product in one fraction and 0.893 g in the second. Analysis on an NMR spectrometer was consistent with the desired products.

Example 7

Preparation of Mono-2-(carboxymethyl) hexadecanamidotetra(ethylene glycol) Mono-4-benzoylbenzyl Ether (Compound 8) and Mono-3-carboxyheptadecanamidotetra(ethylene glycol) Mono-4-benzoylbenzyl Ether (Compound 9)

The tetraethylene glycol (TEG), 7.063 g (36.4 mmol), was azeotroped with 200 ml of toluene for two hours to remove moisture, followed by the removal of excess toluene under vacuum. The TEG residue was then dissolved in 70 ml of anhydrous THF while stirring under argon on an ice bath. Sodium hydride, 1.45 g of a 60% mixture in mineral oil (36.3 mmol), was added and the mixture was stirred 1 hour at room temperature. BMBP, 5.0 g (18.2 mmol), prepared according to the general method described in Example 2, was added and the mixture was stirred 16 hours at room temperature under argon. The reaction was quenched with aqueous ammonium chloride (9 g in 40 ml of water) and the organic solvent was removed under vacuum. The residue was dissolved in saturated brine, extracted with chloroform, and the resulting organic extracts were dried over sodium sulfate. The product was isolated as a viscous oil by adding the chloroform solution to diethyl ether. The crude product, 7.6 g, was used without additional purification.

The entire product from above was dissolved in 200 ml of methylene chloride, followed by the addition of 3.96 g (39.1 mmol) of TEA. The mixture was cooled to 4° C. under argon and 3.35 g (29.2 mmol) of MsCl were added. After 6 hours, an additional 1 ml each of TEA and MsCl were added and the reaction was left to stir for 16 hours to insure complete reaction. The precipitated salts were removed by filtration and the solvent was removed under vacuum. The residue was dissolved in toluene and filtered to remove solids, followed by evaporation under vacuum. No further purification of the product was done at this point.

The entire mesylate product from above was dissolved in 50 ml of THF in a thick-walled glass tube, followed by the addition of 50 ml of concentrated ammonium hydroxide. The tube was sealed and the two phase mixture was stirred vigorously at 65° C. for 16 hours. The solvent was removed under vacuum and the resulting residue was dissolved in 20 ml of chloroform. After drying over sodium sulfate, the product was precipitated by addition of the chloroform solution to diethyl ether resulting in approximately 4.5 g of a brown viscous oil. A portion of the product, approximately 1 g, was purified by silica gel flash chromatography using a solvent gradient of ether/hexane/acetic acid (75/25/1 v/v), followed by chloroform/acetone/acetic acid (60/40/1 v/v), and chloroform/ethanol/water/acetic acid (85/15/1/1 v/v). A total of 220 mg of purified product were isolated. Analysis on an NMR spectrometer was consistent with the desired product.

The amine product from above, 0.220 g (0.568 mmol), and TEA, 63 mg (0.623 mmol), were dissolved in 20 ml of methylene chloride, followed by the addition of 0.185 g (0.625 mmol) of TDSA. The reaction mixture was stirred 48 hours at room temperature under argon. The solvents were removed under vacuum and the resulting oil was purified by silica gel flash chromatography using an chloroform/methanol/water/acetic acid (85/15/1/1 v/v). The appropriate fractions were pooled, evaporated, redissolved in chloroform, and dried over sodium sulfate. Evaporation of solvent gave 234 mg of a waxy solid as a mixture of regioisomers resulting from opening of the anhydride ring. Analysis on an NMR spectrometer was consistent with the desired products.

Example 8

Preparation of N-[2-(4-Benzoylbenzyloxy)ethyl]-2-(carboxymethyl)hexadecanamide (Compound 10) and N-[2-(4-Benzoylbenzyloxy)ethyl]-3-carboxyheptadecanamide (Compound 11)

Anhydrous ethanolamine, 1.00 g (16.4 mmol), was dissolved in 5 ml of anhydrous THF with stirring under argon. Sodium hydride, 0.655 g (16.4 mmol) of a 60% mineral oil dispersion, was added as a solid followed by an additional 5 ml of anhydrous THF. The resulting mixture was stirred at room for 45 minutes at which time no more hydrogen evolution was observed. The BMBP, 4.50 g (16.4 mmol), prepared according to the general method described in Example 2, was added as a solution in 25 ml of THF over a 30 minute period. The reaction was allowed to stir overnight at room temperature. The reaction was quenched with water and the product was extracted with chloroform. The organic extract was washed with 0.1 N HCl and the aqueous solution was washed one time with chloroform. The aqueous was then evaporated under vacuum, dissolved in 10% methanol in chloroform (v/v) and dried over sodium sulfate. Evaporation of solvent gave 2.62 g of a pale yellow solid which was used without additional purification.

The above amine, 0.625 g (2.14 mmol), and TDSA, 0.467 g (1.57 mmol), were dissolved in 10 ml of methylene chloride, followed by the addition of 660 µl (4.74 mmol) of TEA. The resulting solution was stirred at room temperature for 16 hours to complete the reaction. The product was diluted with water and treated with 5% HCl, followed by separation of the organic layer and drying over sodium sulfate. The solvent was removed under vacuum and the product was purified using silica gel flash chromatography with a solvent gradient of chloroform followed by 2.5% and 5 % (v/v) methanol in chloroform. The appropriate fractions were pooled to give 357 mg of product as a pair of regioisomers resulting from the opening of the anhydride ring. Analysis on an NMR spectrometer was consistent with the desired products.

Example 9

Preparation of N-[12-(Benzoylbenzyloxy)dodecyl]-2-(carboxymethyl)hexadecanamide (Compound 12) and N-[2-(Benzoylbenzyloxy)dodecyl]-3-carboxyheptadecanamide (Compound 13)

1,12-Dodecanediol, 5.0 g (24.7 mmol), was dissolved in 50 ml of anhydrous THF in a dry flask under nitrogen. The sodium hydride, 0.494 g of a 60% dispersion in mineral oil (12.4 mmol), was added in portions over a five minute period. The resulting mixture was stirred at room temperature for one hour. BMBP, 3.40 g (12.4 mmol), prepared according to the general method described in Example 2, was added as a solid along with sodium iodide (0.185 g, 1.23 mmol) and tetra-n-butylammonium bromide (0.398 g, 1.23 mmol). The mixture was stirred at a gentle reflux for 24 hours. The reaction was then cooled, quenched with water, acidified with 5% HCl, and extracted with chloroform. The organic extracts were dried over sodium sulfate and the solvent was removed under vacuum. The product was purified on a silica gel flash chromatography column using chloroform to elute non-polar impurities, followed by elution of the product with chloroform/ethyl acetate (80/20 v/v). Pooling of appropriate fractions and evaporation of solvent gave 3.42 g of product, a 70% yield. Analysis on an NMR spectrometer was consistent with the desired product.

The above alcohol, 1.30 g (3.28 mmol), was dissolved in 13 ml of anhydrous methylene chloride, followed by 0.829 g (8.19 mmol) of TEA and cooling on an ice bath under argon. MsCl, 0.563 g (4.91 mmol), was added dropwise over a five minute period, followed by stirring at room temperature for 16 hours. The reaction was diluted with water, acidified with 5% HCl, and extracted with chloroform. The organic extracts were dried over sodium sulfate and evaporated to give 1.56 g of a yellow oil. This product was used without further purification. Analysis on an NMR spectrometer was consistent with the desired product.

The above mesylate, 1.56 g (3.28 mmol), was dissolved in 25 ml of THF in a thick-walled tube, followed by the addition of 25 ml of ammonium hydroxide. The tube was sealed and the mixture was stirred vigorously for 72 hours at 80° C. The mixture was treated with 200 ml of water and the product was extracted with chloroform. The organic extracts were dried over sodium sulfate and the product was purified on a silica gel flash chromatography column.

The column was eluted with chloroform and chloroform/methanol (95/5 v/v) until the less polar impurities were removed, followed by elution of the desired product using chloroform/methanol/ammonium hydroxide (70/25/5 v/v). Pooling of the ninhydrin and UV active fractions and evaporation of solvent gave 0.526 g of product, a 40% yield. Analysis on an NMR spectrometer was consistent with the desired product.

The above amine, 0.440 g (1.11 mmol), was dissolved in 7 ml of methylene chloride, followed by 0.329 g (1.11 mmol) of TDSA and 0.337 g (3.33 mmol) of TEA. The resulting mixture was stirred at room temperature for 36 hours. The reaction was then diluted with water, acidified with 5% HCl, and extracted with chloroform. The organic extracts were dried over sodium sulfate and the residue after evaporation was purified on silica gel flash chromatography. A solvent gradient of chloroform, 2.5% methanol in chloroform (v/v), and 5% methanol in chloroform (v/v) was used to elute the product. A total of 378 mg of product were isolated as a partially resolved pair of regioisomers resulting from opening of the anhydride ring. Analysis on an NMR spectrometer was consistent with the desired products.

Example 10

Preparation of N-[3-(4-Benzoylbenzamido)propyl]-2-(carboxymethyl)hexadecanamide (Compound 14) and N-[3-(4-Benzoylbenzamido)propyl]-3-carboxyheptadecanamide (Compound 15)

1,3-Diaminopropane, 1.910 kg (25.77 mol), was placed in a 12 liter Morton flask and diluted with 1000 ml of methylene chloride. After cooling to below 10° C. on an ice bath, a solution of 1.005 kg (5.175 mol) of t-butyl phenyl carbonate in 250 ml of methylene chloride was added slowly to the diamine while keeping the temperature below 15° C. at all times. Once the addition was complete, the mixture was warmed to room temperature for 2 hours to complete the reaction. The reaction was further diluted with 900 ml of methylene chloride, followed by the addition of 500 g of ice and a slow addition of 2500 ml of 2.2 N NaOH. The organic layer was separated and the basic aqueous solution was extracted with 3×1250 ml of methylene chloride, keeping each extract separate. Each of these separate extracts was successively washed with 1250 ml of 0.6 N NaOH, beginning with the first extract and proceeding to the last. This wash procedure was repeated and the organic extracts were combined and dried over sodium sulfate. Evaporation of solvent yielded 825 g of product for a 92% yield. This product was used without any further purification. Analysis on an NMR spectrometer was consistent with the desired product.

The above amine, 0.774 g (4.44 mmol), was diluted with 20 ml of anhydrous methylene chloride, followed by the addition of 1.24 g (12.3 mmol) of TEA and a dropwise addition of 10 ml of anhydrous methylene chloride containing of 1.0 g (4.09 mmol) of BBA-Cl, prepared according to the general method described in Example 1, After stirring 1.5 hours at room temperature, the reaction was diluted with water and acidified with 1 N HCl. The product was extracted with chloroform and the organic extracts were dried over sodium sulfate. Silica gel flash chromatography using chloroform/methanol (90/10 v/v) gave 1.68 g of product, slightly greater than theoretical because of solvent residues. Mass spectral analysis confirmed the desired product.

The above product, 1.5 g (3.95 mmol), was dissolved in 10 ml of trifluoroacetic acid under a nitrogen atmosphere. After stirring 3 hours at room temperature to remove the t-butyloxycarbonyl (t-BOC) protecting group, the solvent was removed under reduced pressure and the product was purified using silica gel flash chromatography. After removal of the less polar impurities with chloroform/methanol (90/10 v/v), the eluting solvent was switched to chloroform/methanol/ammonium hydroxide (70/25/5 v/v) for isolation of the desired product. Pooling of the appropriate fractions and evaporation of solvent gave 1.77 g of product. Analysis on an NMR spectrometer was consistent with the desired product.

A portion of above amine product, 0.500 g (1.77 mmol), was dissolved in 10 ml of anhydrous methylene chloride under an argon atmosphere. TEA, 0.197 g (1.95 mmol), was added, followed by 0.577 g (1.95 mmol) of TDSA. The reaction was stirred for four hours at room temperature. The mixture was diluted with water, extracted with methylene chloride, and the organic extracts were dried over sodium sulfate. After vacuum removal of solvents, the product was purified by silica gel flash chromatography using a chloroform/methanol/acetic acid/water (85/15/1/1 v/v) system. A repeat chromatography using a 0→5% methanol in chloroform (v/v) system gave a more pure product. A total of 0.259 g of product (25% yield) were isolated as a pair of regioisomers resulting from opening of the anhydride ring. Analysis on an NMR spectrometer was consistent with the desired products.

Example 11

Preparation of N-(3-Benzoylphenyl)-2-(carboxymethyl)hexadecanamide (Compound 16) and N-(3-Benzoylphenyl)-3-carboxyheptadecanamide (Compound 17)

The 3-aminobenzophenone, 0.500 g (2.53 mmol), was dissolved in 5.0 ml of dry DMF along with 0.512 g (5.06 mmol) of TEA and 0.030 g (0.25 mmol) of 4-dimethylaminopyridine. While stirring under argon, 0.826 g (2.79 mmol) of TDSA were added and the resulting solution was stirred at 45° C. overnight. The reaction was diluted with water and the desired product was extracted with chloroform. After drying over sodium sulfate, the solvent was removed and the product was purified on silica gel flash chromatography. The less polar impurities were eluted with chloroform and the product was eluted with a 2.5→5.0% methanol in chloroform (v/v) gradient. A total of 1.048 g of product were isolated with a partial resolution of the two regioisomers resulting from opening of the anhydride ring system. Analysis on an NMR spectrometer was consistent with the desired products.

Example 12

Preparation of N-(4-Benzoylphenyl)-2-(carboxymethyl)hexadecanamide (Compound 18) and N-(4-Benzoylphenyl)-3-carboxyheptadecanamide (Compound 19)

The 4-aminobenzophenone, 0.500 g (2.53 mmol), was dissolved in 7.0 ml of dry DMF along with 0.512 g (5.06 mmol) of TEA and 0.030 g (0.25 mmol) of 4-dimethylaminopyridine. While stirring under argon, 0.826 g (2.79 mmol) of TDSA were added and the resulting solution was stirred at 55° C. for 80 hours. At this time, thin layer chromatography (TLC) revealed partial conversion to a less polar UV active product. The reaction was diluted with water and the desired product was extracted with chloroform. After drying over sodium sulfate, the solvent was removed and the product was purified on silica gel flash chromatography. The less polar impurities were eluted with chloroform and the product was eluted with a 2.5→5.0% methanol in chloroform (v/v) gradient. A total of 0.753 g of product were isolated with a partial resolution of the two regioisomers resulting from opening of the anhydride ring system. Analysis on an NMR spectrometer was consistent with the desired products.

Example 13

Preparation of Monohexadecanamidopoly(ethylene glycol)$_{200}$ Mono-4-benzoylbenzyl Ether (Compound 20)

Compound 5, 0.914 g (2.32 mmol), prepared according to the general method described in Example 5, was dissolved in 10 ml of anhydrous chloroform with stirring under argon. TEA, 0.516 g (5.10 mmol), was added followed by the slow dropwise addition of 0.701 g (2.55 mmol) of palmitoyl chloride. The resulting mixture was stirred at room temperature overnight. The reaction was diluted with water and the product was extracted with chloroform. After drying over sodium sulfate, the solvent was removed under vacuum and the product was purified by silica gel chromatography. A chloroform/methanol (95/5) solvent was used to elute the product, yielding 382 mg of a viscous oil. Analysis on an NMR spectrometer was consistent with the desired product.

Example 14

Preparation of Mono-3-Carboxypropanamidopoly (ethylene glycol)200 Mono-4-benzoylbenzyl Ether (Compound 21)

Compound 5, 0.500 g (1.27 mmol), prepared according to the general method described in Example 5, was dissolved in 5 ml of anhydrous chloroform along with 0.14 g (1.40 mmol) of succinic anhydride. After solution was complete, 0.141 g (1.39 mmol) of TEA were added with stirring under argon. The resulting mixture was stirred at room temperature for 24 hours. The solvent was then removed under vacuum and the product was purified on a silica gel flash chromatography column using a chloroform solvent, followed by a chloroform/methanol (95/5 to 90/10 v/v) solvent gradient. Pooling of appropriate fractions and evaporation of solvent gave 447 mg of a viscous oil. Analysis on an NMR spectrometer was consistent with the desired product.

Example 15

Preparation of Hexadecyl 4-Benzoylbenzyl Ether (Compound 22)

1-Hexadecanol, 5.0 g (20.6 mmol), was dissolved in 10 ml of anhydrous THF with warming, followed by slow addition of 0.840 g (21.0 mmol) of a 60% dispersion of NaH in mineral oil. Once the hydrogen evolution was complete, 6.35 g (23.1 mmol) of BMBP, prepared according to the general method described in Example 2, were added. The reaction mixture was stirred at 50° C. under argon for one hour and then at room temperature for 16 hours. After this time the reaction was quenched with water and the product was extracted with chloroform. After drying over sodium sulfate, the solvent was removed under vacuum and the residue was purified by silica gel flash chromatography using a hexane/ether (90/10) solvent. Appropriate fractions were pooled and evaporated to give 8.01 g of a waxy solid, an 88.9% yield. Analysis on an NMR spectrometer was consistent with the desired product.

Example 16

Preparation of Poly(ethylene glycol)$_{200}$ Monohexadecyl Mono-4-benzoylbenzyl Ether (Compound 23)

Compound 3, 1.00 g (2.54 mmol), prepared according to the general method described in Example 3, was dissolved in 10 ml of anhydrous THF under an argon atmosphere. Sodium hydride, 0.112 g (2.80 mmol) of a 60% dispersion in mineral oil, was added in portions while stirring on an ice bath. The mixture was allowed to stir 20 minutes at room temperature, followed by the addition of 0.776 g (2.54 mmol) of 1-bromohexadecane. The mixture was stirred overnight at room temperature. The reaction was quenched with water and the product was extracted with chloroform. After drying over sodium sulfate and removal of solvent, the product was purified by silica gel flash chromatography using a chloroform/methanol/acetic acid/water (85/15/1/1 v/v) solvent as eluent. The appropriate fractions were pooled to give 1.357 g of product, an 86% yield. Analysis on an NMR spectrometer was consistent with the desired product.

Example 17

Preparation of Poly(ethylene glycol)$_{200}$ Mono-15-carboxypentadecyl Mono-4-benzoylbenzyl Ether (Compound 24)

10-Hydroxyhexadecanoic acid, 0.785 g (2.88 mmol), was dissolved in 20 ml of anhydrous DMF in a dry flask under argon. Sodium hydride, 0.260 g (6.5 mmol) of a 60% dispersion in mineral oil, was then added and the resulting slurry was stirred at 60° C. for four hours. After this time, Compound 4, 1.24 g (2.62 mmol), prepared according to the general method described in Example 4, was added as a solution in 7 ml of DMF. The resulting slurry was stirred at room temperature for 72 hours. After this time, the reaction was quenched with water and the product was extracted with chloroform. After drying over sodium sulfate, the product was purified on a silica gel flash chromatography column. The column was eluted with chloroform/methanol (95/5 v/v) until the less polar impurities were removed, followed by elution of the product with chloroform/methanol/acetic acid/water (90/10/1/1 v/v). The appropriate fractions were pooled and evaporated to yield 1.24 g of product, a 74% yield. Analysis on an NMR spectrometer was consistent with the desired product.

Example 18

Preparation of Mono-15-carboxypentadecanamidopoly(ethylene glycol)$_{200}$ Mono-4-benzoylbenzyl Ether (Compound 25)

Hexadecanedioic acid, 0.500 g (1.75 mmol), was dissolved in 5 ml of anhydrous DMF with stirring under an argon atmosphere. N-Hydroxysuccinimide, 0.442 g (3.84 mmol) and dicyclohexylcarbodiimide, 1.44 g (6.98 mmol), were added and the mixture was stirred for six hours at room temperature. The resulting solid was removed by filtration and the filter cake was washed with 1 ml of DMF. The solution was then reacted with 0.747 g (1.90 mmol) of Compound 5, prepared according to the general method described in Example 5, dissolved in 5 ml of DMF and 0.389 g (3.84 mmol) of TEA. After stirring two hours at room temperature, TLC showed complete consumption of the starting amine. The product was purified on a silica gel flash chromatography column by eluting less polar impurities using chloroform and elution of the desired product using a chloroform/methanol/acetic acid/water (85/15/1/1 v/v) solvent. The appropriate fractions were pooled and evaporated to give 1.356 g of product. Analysis on an NMR spectrometer was consistent with the desired product.

Example 19

Preparation of N-[3-Methacrylamido)propyl]-2-(carboxymethyl)hexadecanamide (Compound 26) and N-[3-Methacrylamido)propyl]-3-carboxyheptadecanamide (Compound 27)

N-(3-Aminopropyl)methacrylamide hydrochloride (APMA-HCl), 6.064 (33.9 mmol), was dissolved in anhydrous methylene chloride along with 10.24 g (101 mmol) of TEA. TDSA, 10.0 g (33.7 mmol), was immediately added and the mixture was stirred 48 hours at room temperature with moisture protection from a drying tube. After this time, the reaction was acidified with 1 N HCl, extracted with chloroform, and dried over sodium sulfate. The product was purified on a silica gel chromatography column using a chloroform/methanol/acetic acid/water (85/15/1/1 v/v) solvent. The appropriate fractions were pooled, 100 ppm of phenothiazine were added, and the solvent was removed under reduced pressure to give 16.0 g of product as a pair of regioisomers resulting from opening of the anhydride ring. Analysis on an NMR spectrometer was consistent with the desired products.

Example 20

Preparation of N-[3-(4-Benzoylbenzamido)propyl] methacrylamide (BBA-APMA) (Compound 28)

APMA-HCl, 120.0 g (0.672 mol), was suspended in 800 ml of chloroform along with 25 mg of phenothiazine. The solution was cooled to below 10° C., followed by the addition of 172.5 g (0.705 mol) of BBA-Cl, prepared according to the general method described in Example 1. A solution of 150.3 g (1.49 moles) of TEA in 50 ml of chloroform was prepared and the solution was added dropwise to the above suspension over a 1–1.5 hour time period while stirring on an ice bath. After completion of the addition, the ice bath was removed and the solution was stirred for 2.5 hours to complete the reaction. The mixture was then washed with 600 ml of 0.3 N HCl followed by 2×300 ml of 0.07 N HCl. The chloroform solution was then dried over sodium sulfate and the product was recrystallized twice using a toluene/chloroform (4/1 v/v) mixture. Phenothiazine, 25 mg, was added prior to the second recrystallization to prevent premature polymerization. The yield was 212 g (90% yield) with a melting point of 147–151° C. Analysis on an NMR spectrometer was consistent with the desired product.

Example 21

Preparation of N-(2-Mercaptoethyl)-3,5-bis(4-benzoylbenzyloxy)benzamide (Compound 29)

A photoactivatable chain transfer reagent was prepared in the following manner, and used in the manner described in Examples 22 and 24. 3,5-Dihydroxybenzoic acid, 46.2 g (0.30 moles), was weighed into a 250 ml flask equipped with a Soxhlet extractor and condenser. Methanol, 48.6 ml, and concentrated sulfuric acid, 0.8 ml, were added to the flask and 48 g of 3A molecular sieves were placed in the Soxhlet extractor. The extractor was diluted with methanol and the mixture was heated at reflux overnight. Gas chromatographic analysis on the resulting product showed a 98% conversion to the desired methyl ester. The solvent was removed under reduced pressure to give approximately 59 g of crude product. This product was used in the following step without further purification. A small sample was purified for NMR analysis, resulting in a spectrum consistent with the desired product.

The entire methyl ester product from above was placed in a 2 liter flask with overhead stirrer and condenser, followed by the addition of 173.25 g (0.63 mol) of BMBP, prepared according to the general method described in Example 2, 207 g (1.50 mol) of potassium carbonate, and 1200 ml of acetone. The resulting mixture was then refluxed overnight to give complete reaction as indicated by TLC. The solids were removed by filtration and the acetone was evaporated under reduced pressure to give 49 g of crude product. The solids were diluted with 1 liter of water and extracted with 3×1 liter of chloroform. The extracts were combined with the acetone soluble fraction and dried over sodium sulfate, yielding 177 g of crude product. The product was recrystallized from acetonitrile to give 150.2 g of a white solid, a 90% yield for the first two steps. Melting point of the product was 131.5° C. (DSC) and analysis on an NMR spectrometer was consistent with the desired product.

The methyl 3,5-bis(4-benzoylbenzyloxy)benzoate, 60.05 g (0.108 mol), was placed in a 2 liter flask, followed by the addition of 120 ml of water, 480 ml of methanol, and 6.48 g (0.162 mol) of sodium hydroxide. The mixture was heated at reflux for three hours to complete hydrolysis of the ester. After cooling, the methanol was removed under reduced pressure and the sodium salt of the acid was dissolved in 2400 ml of warm water. The acid was precipitated using concentrated hydrochloric acid, filtered, washed with water, and dried in a vacuum oven to give 58.2 g of a white solid (99% yield). Melting point on the product was 188.3° C.

(DSC) and analysis on an NMR spectrometer was consistent with the desired product.

The 3,5-bis(4-benzoylbenzyloxy)benzoic acid, 20.0 g (36.86 mmol), was added to a 250 ml flask, followed by 36 ml of toluene, 5.4 ml (74.0 mmol) of thionyl chloride, and 28 µl of DMF. The mixture was refluxed for four hours to form the acid chloride. After cooling, the solvent and excess thionyl chloride were removed under reduced pressure. Residual thionyl chloride was removed by four additional evaporations using 20 ml of chloroform each. The crude material was recrystallized from toluene to give 18.45 g of product, an 89% yield. Melting point of product was 126.9° C. (DSC) and analysis on an NMR spectrometer was consistent with the desired product.

The 2-aminoethanethiol hydrochloride, 4.19 g (36.7 mmol), was added to a 250 ml flask equipped with an overhead stirrer, followed by 15 ml of chloroform and 10.64 ml (76.5 mmol) of TEA. After cooling the amine solution on an ice bath, a solution of 3,5-bis(4-benzoylbenzyloxy) benzoyl chloride, 18.4 g (32.8 mmol), in 50 ml of chloroform was added dropwise over a 50 minute period. Cooling on ice was continued 30 minutes, followed by warming to room temperature for two hours. The product was diluted with 150 ml of chloroform and washed with 5×250 ml of 0.1 N hydrochloric acid. The product was dried over sodium sulfate and recrystallized twice from toluene/hexane (15/1 v/v) to give 13.3 g of product, a 67% yield. Melting point on the product was 115.9° C. (DSC) and analysis on an NMR spectrometer was consistent with the desired product.

Example 22

Preparation of a Photoreactive Endpoint Copolymer of Acrylamide and Fatty Acid Monomers (Compound 30)

Acrylamide, 0.640 g (9.00 mmol), was dissolved in 9 ml of THF, followed by the addition of 0.299 g (0.68 mmol) of Compounds 26 and 27, prepared according to the general method described in Example 19, 0.060 g (0.10 mmol) of Compound 29, prepared according to the general method described in Example 21, 9 µl (0.060 mmol) of N,N,N',N'-tetramethylethylenediamine (TEMED), and 0.049 g (0.30 mmol) of 2,2'-azobisisobutyronitrile (AIBN). The solution was sparged two minutes with helium, two minutes with argon, and was then sealed and heated overnight at 55° C. The resulting suspension was diluted with 5 ml of additional THF and added to diethyl ether, followed by filtration to isolate the solid. After drying in a vacuum oven, 0.966 g of a white solid were isolated. Analysis of the polymer revealed 0.073 mmol of BBA per gram of polymer.

Example 23

Preparation of a Photoreactive Random Copolymer of Acrylamide and Fatty Acid Monomers (Compound 31)

Acrylamide, 0.657 g (9.24 mmol), was dissolved in 9 ml of THF, followed by the addition of 0.307 g (0.70 mmol) of Compounds 26 and 27, prepared according to the general method described in Example 19, 0.036 g (0.10 mmol) of Compound 28, prepared according to the general method described in Example 20, 9 µl (0.060 mmol) of TEMED, and 0.026 g (0.16 mmol) of AIBN. The solution was sparged two minutes with helium, two minutes with argon, and was then sealed and heated overnight at 55° C. The resulting suspension was diluted with 5 ml of additional THF and added to diethyl ether, followed by filtration to isolate the solid. After drying in a vacuum oven, 0.997 g of a white solid were isolated. Analysis of the polymer revealed 0.086 mmol of BBA per gram of polymer.

Example 24

Preparation of a Photoreactive Endpoint Copolymer of N-Vinylpyrrolidone and Fatty Acid Monomers (Compounds 32A–C)

N-Vinylpyrrolidone, 0.915 g (8.23 mmol), was dissolved in 3 ml of THF, followed by the addition of 0.271 g (0.618 mmol) of Compounds 26 and 27, prepared according to the general method described in Example 19, 0.070 g (0.116 mmol) of Compound 29, prepared according to the general method described in Example 21, 1 µl (0.01 mmol) of TEMED, and 0.057 g (0.347 mmol) of AIBN. This composition was designed to make TDSA 7 mole % of the monomers in the reaction mixture. The solution was sparged two minutes with helium, two minutes with argon, and was then sealed and heated overnight at 55° C. The polymer was precipitated by the addition of diethyl ether, followed by isolation with filtration. After drying in a vacuum oven, 1.10 g of a white solid were isolated. Analysis of Compound 32A revealed 0.109 mmol of BBA per gram of polymer.

The above procedure was followed using the following quantities of reagents in 4 ml of THF: N-vinylpyrrolidone, 0.433 g (3.90 mmol); Compounds 26 and 27, 0.507 g (1.16 mmol) Compound 29, 0.060 g (0.10 mmol); TEMED, 3 µl (0.02 mmol); and AIBN, 0.049 g (0.298 mmol). This composition was designed to make TDSA 23 mole % of the monomers in the reaction mixture. After isolation following the above procedure, 0.808 g of a white solid were isolated. Analysis of Compound 32B revealed 0.083 mmol of BBA per gram of polymer.

The above procedure was followed using the following quantities of reagents in 3 ml of THF: N-vinylpyrrolidone, 0.181 g (1.63 mmol); Compounds 26 and 27, 0.759 g (1.73 mmol); Compound 29, 0.060 g (0.10 mmol); TEMED, 1 µl (0.01 mmol); and AIBN, 0.049 g (0.298 mmol). This composition was designed to make TDSA 50 mole % of the monomers in the reaction mixture. After isolation following the above procedure, 0.705 g of a white solid were isolated. Analysis of Compound 32C revealed 0.102 mmol of BBA per gram of polymer.

Example 25

Preparation of a Photoreactive Random Copolymer of N-Vinylpyrrolidone and Fatty Acid Monomers (Compounds 33A–D)

N-Vinylpyrrolidone, 0.749 g (6.74 mmol), was dissolved in 8.8 ml of THF, followed by the addition of 0.224 g (0.511 mmol) of Compounds 26 and 27, prepared according to the general method described in Example 19, 0.027 g (0.077 mmol) of Compound 28, prepared according to the general method described in Example 20, 1 µl (0.01 mmol) of TEMED, and 0.019 g (0.116 mmol) AIBN. This composition was designed to make TDSA 7 mole % of the monomers in the reaction mixture. The solution was sparged two minutes with helium, two minutes with argon, and was then sealed and heated overnight at 55° C. The polymer was precipitated by the addition of diethyl ether, followed by isolation with filtration. After drying in a vacuum oven, 0.353 g of a white solid were isolated. Analysis of the Compound 33A revealed 0.112 mmol of BBA per gram of polymer.

The above procedure was followed using the following quantities of reagents in 3 ml of THF: N-vinylpyrrolidone, 0.362 g (3.26 mmol); Compounds 26 and 27, 0.621 g (1.42 mmol); Compound 28, 0.017 g (0.049 mmol); TEMED, 1 µl (0.01 mmol); and AIBN, 0.012 g (0.073 mmol). This composition was designed to make TDSA 30 mole % of the monomers in the reaction mixture. After isolation following the above procedure, 0.770 g of a white solid were isolated. Analysis of Compound 33B revealed 0.052 mmol of BBA per gram of polymer.

The above procedure was followed using the following quantities of reagents in 3 ml of THF: N-vinylpyrrolidone, 0.196 g (1.76 mmol); Compounds 26 and 27, 0.791 g (1.80 mmol); Compound 28, 0.013 g (0.037 mmol); TEMED, 1 µl (0.01 mmol); and AIBN, 0.009 g (0.055 mmol). This composition was designed to make TDSA 50 mole % of the monomers in the reaction mixture. After isolation following the above procedure, 0.708 g of a white solid were isolated. Analysis of Compound 33C revealed 0.048 mmol of BBA per gram of polymer.

The above procedure was followed using the following quantities of reagents in 7 ml of THF: N-vinylpyrrolidone, 0.188 g (1.69 mmol); Compounds 26 and 27, 1.792 g (4.09 mmol); Compound 28, 0.020 g (0.057 mmol); TEMED, 1 µl (0.01 mmol); and AIBN, 0.014 g (0.085 mmol). This composition was designed to make TDSA 70 mole % of the monomers in the reaction mixture. After isolation following the above procedure, 0.879 g of a white solid were isolated. Analysis of Compound 33D revealed 0.058 mmol of BBA per gram of polymer.

Example 26

Preparation of a Photoreactive Siloxane Copolymer Containing Fatty Acid Ligands (Compound 34)

An aminopropylmethylsiloxane-dimethylsiloxane copolymer, 5.00 g of a 6–7 mole % amine monomer content, was dissolved in 50 ml of dry methylene chloride, followed by the addition of 0.79 g (7.81 mmol) of TEA. BBA-CL, 0.19 g (0.78 mmol), prepared according to the general method described in Example 1, was then added and the mixture was stirred 3 hours at room temperature. TDSA, 0.924 g (3.12 mmol), was then added and the solution was stirred 24 hours at room temperature. The reaction was then diluted with water and the pH was adjusted to approximately 6 using 0.1 N HCl. The organic layer was removed and dried over sodium sulfate. The solvent was removed under reduced pressure and the resulting oil was diluted with hexane. The precipitate was removed by filtration and evaporation of the solvent gave 4.75 g of a viscous oil. Analysis of the polymer revealed 0.013 mmol of BBA per gram of polymer.

Example 27

Fatty Acid Immobilization on an Amine Derivatized Surface

A polymer surface is derivatized by plasma treatment using a 3/1 mixture of methane and ammonia gases (v/v). (See, e.g., the general method described in U.S. Pat. No. 5,643,580). A mixture of methane (490 SCCM) and ammonia (161 SCCM) are introduced into the plasma chamber along with the polymer part to be coated. The gases are maintained at a pressure of 0.2–0.3 torr and a 300–500 watt glow discharge is established within the chamber. The sample is treated for a total of 3–5 minutes under these conditions. Formation of an amine derivatized surface is verified by surface analysis using Electron Spectroscopy for Chemical Analysis (ESCA) and Time of Flight Secondary Ion Mass Spectrometry (TOF-SIMS).

TDSA is dissolved at a concentration of 30 mg/ml in a solvent compatible with both the polymer substrate and the anhydride. TEA, 1.5 equivalents relative to the anhydride, are added to the solution and the final mixture is allowed to incubate with the amine derivatized surface for 24 hours at room temperature to permit maximal coupling of the fatty acid to the surface. The final surface is then washed with fresh solvent to remove all unreacted materials and the final wash is a dilute acid wash to remove any remaining TEA.

Example 28

Surface Modification of Selected Substrates with Reagents

Three polymers commonly-used as biomaterials were surface-modified with novel compounds described above. The polymer substrates included polyethylene (PE), polyvinylchloride (PVC), and polyurethane (PU). These polymers were obtained as flat sheets and used as 1×1 cm squares, 1 cm circular disks or obtained in cylindrical form (tubes or rods) and used as short segments. The shape and size of the part was chosen based on the particular assay to be conducted with the coated substrates.

Coating solutions were prepared by dissolving the reagents at concentrations ranging from 1–15 mg/ml in neat isopropanol (IPA) or deionized water/IPA solutions. The reagents were applied to the polymer substrates using dip coating methods. Parts were suspended vertically, immersed in the solution at 2 cm/sec, allowed to dwell for five seconds, and then withdrawn at a rate of 0.1 cm/sec. After removal of the substrate from the coating solution, it was air dried until the solvent was no longer visible, often within about 1 minute. The substrate with the coating was then suspended midway between two opposed Dymax UV curing lamps, each outfitted with a Heraeus Q402Z4 bulb. At the distance of placement of the lamps, the parts received approximately 1.5 mW/cm$^2$ in the wavelength range 330–340 nm. The substrate was rotated at 3 rpm during the two minutes of illumination to ensure that the surface was evenly bathed in light. After illumination, the parts were removed from the lamp chamber and washed in IPA, using two sequential 30-minute washes in fresh solvent. The coated samples were then stored in the dark at ambient temperature until used.

Example 29

Surface Analysis of Polymer Substrates Modified with Compounds 8, 9, 18, 19, 32, and 33.

Three different techniques (staining, ESCA, and TOF-SIMS) were used to evaluate the surfaces of modified substrates to confirm the presence and uniformity of the compounds.

PE and PVC flat materials were modified with heterobifunctional reagents (Compounds 8, 9, 18, 19) and polymeric reagents (Compounds 32 and 33, having varying monomer compositions). Reagents were prepared in IPA at 1.0 mg/ml and applied using the methods described in Example 28.

First, the coated materials were stained with Toluidine Blue ), a positively-charged, visible-wavelength dye. Samples were immersed in a solution of the dye (0.02% w/v in water) for 30 seconds, removed from solution, and rinsed with DI water. This staining protocol was useful for identifying qualitatively the presence of each of the reagents on the material surface. The results of the dye binding suggested that the surface modification procedures were successful in immobilizing the reagents on the substrate surfaces. There was some variability in the darkness of the stain, both from different reagents on the same material and for the same reagents on different materials. The staining was grossly uniform to the naked eye over the surfaces of the material, suggesting that the reagent was not pooling or segregating when applied to the surface and that the coverage of the surface was relatively uniform.

ESCA was used to analyze quantitatively the surface chemical composition of the modified substrates. PE and PVC modified with heterobifunctional reagents (Compounds 8, 9, 18, 19) and polymeric reagents (Compounds 32 and 33, having varying molar compositions) were analyzed with a Perkin Elmer Model 5400 ESCA system using monochromatic Al X-rays with analysis at a 65 degree takeoff angle. Survey spectra were collected to calculate the atomic concentrations in the surface.

The results of the ESCA measurements (Tables 1 and 2) on the surface modified materials were useful for indicating the presence and chemical composition of the coatings. For the PVC substrate, the atomic concentration of the chlorine atom (Cl) was used to determine whether the coating masked the substrate material. By comparing the amounts of Cl detected on the surface of the PVC after modification, it was clear that the Cl was greatly reduced on the surface-modified substrates. Together with the results of the dye binding described above, this suggested that the reagents covered the surface completely, but were thin enough to detect the underlying substrate. For the PE substrate, which in the uncoated state should have an atomic concentration of 100% carbon (as ESCA cannot detect H atoms), the modified and unmodified samples could simply be compared using the carbon concentration. On all of the modified samples the carbon concentration was reduced by about 20%. It was also evident that nitrogen was present on the surfaces of the modified PE and PVC, but not on the uncoated surfaces. This was indicative of the nitrogen in each of the reagents. Finally, the similarity in the atomic concentrations of C, O, and N on the surfaces of PE and PVC samples modified with each compound supports the presence and completeness of the coating.

TABLE 1

Atomic Concentration summary for PE samples (atomic %).

| Sample | [C] | [O] | [N] | [Cl] | [Si] | [Na] |
|---|---|---|---|---|---|---|
| Uncoated | 100 | — | — | — | — | — |
| Compound 33D | 83.4 | 10.5 | 6.2 | — | — | — |
| Compound 33C | 80.9 | 11.3 | 7.8 | — | — | — |
| Compound 33B | 80.7 | 11.1 | 8.3 | — | — | — |
| Compound 32C | 80.3 | 12.4 | 7.3 | — | — | — |
| Compound 32B | 79.3 | 12.1 | 8.1 | — | 0.5 | — |
| Compounds 18, 19 | 83.8 | 13.9 | 2.3 | — | — | — |
| Compounds 8, 9 | 81.4 | 16.8 | 1.6 | — | — | 0.2 |

TABLE 2

Atomic Concentration Summary for PVC samples (atomic %).

| Sample | [C] | [O] | [N] | [Cl] | [Si] | [Na] |
|---|---|---|---|---|---|---|
| Uncoated | 74.2 | 7.5 | — | 17.6 | — | 0.5 |
| Compound 33D | 80.4 | 11.5 | 6.2 | 1.9 | — | — |
| Compound 33C | 78.8 | 12.1 | 8.8 | 0.4 | — | — |
| Compound 33B | 77.8 | 11.6 | 9.1 | 1.3 | — | 0.1 |
| Compound 32C | 79.9 | 12.4 | 6.8 | 0.8 | — | — |
| Compound 32B | 77.6 | 12.2 | 9.1 | 0.4 | 0.7 | — |
| Compounds 18, 19 | 83.4 | 12.8 | 2.4 | 1.4 | — | — |
| Compounds 8, 9 | 79.7 | 17.4 | 1.4 | 1.1 | — | 0.3 |

TOF-SIMS was conducted to ensure that the coatings were located on the outermost surface of the substrates. TOF-SIMS is sensitive to the chemical structure within the outer 10 Å of a surface. TOF-SIMS was performed by Physical Electronics (Eden Prairie, Minn.) using a Physical Electronics model number 7200 instrument. Positive- and negative-ion spectra were recorded for each of the surfaces. In addition, scans of the surface were used to determine the uniformity of chemical fragments which were indicative of the coatings (independent of the substrate chemistry). The surfaces (substrates and coatings) analyzed by TOF-SIMS were the same as those analyzed by ESCA, described above. For the coated substrates, the TOF-SIMS spectra were substantially different from the spectra for the uncoated PE or PVC material. For example, there were many chemical fragments containing nitrogen, which is not present in either of the base materials. There were many high molecular weight fragments in the positive ion spectra (between 200 and 600 mass/charge units) associated with the heterobifunctional reagents (Compounds 8, 9 and 18, 19). The polymer-based reagents (Compounds 32, 33) had regular repeating fragment fingerprints indicative of the polymer backbone. Also confirming that the reagents were present on the surfaces of the materials, was that the fragment patterns for each compound were similar on the two different substrates. In addition, the scans of the surface to detect the presence of peaks uniquely associated with the coating reagents indicated that the reagents were relatively uniformly distributed over the surface of the substrate, further confirming the results of the Toluidine Blue O staining tests described previously.

Example 30

Human Serum Albumin (HSA) Adsorption from Buffer and Platelet Poor Plasma

Adsorption of human serum albumin (HSA) from single protein buffer solution and from diluted human platelet poor plasma (PPP) onto the polymer materials was quantified using radiolabeled protein. Fatty acid-free HSA (Sigma Chemical, St. Louis Mo.) was radiolabeled with $^3$H using sodium borohydride techniques (Means and Feeney, *Biochemistry* 7, 2192 (1968)). Buffer solutions of HSA were prepared by dissolving unlabeled HSA to a concentration of 0.1 mg/ml in Tris-saline (TN) buffer solution (50 mM Tris, 150 mM NaCl, pH 7.5). The resulting solution was then spiked with an aliquot of the $^3$H-HSA such that the specific activity was approximately 1000 dpm/μg HSA for the total solution. Plasma solutions were prepared using a commercially-available PPP (George King Biomedical; Overland Park, Ky.) prepared from blood anticoagulated with sodium citrate (3.8%). Just prior to an adsorption experiment, the PPP was diluted 4:1 with phosphate buffered saline (10 mM phosphate, 150 mM NaCl, pH 7.4; PBS) and then spiked with the radiolabeled HSA such that the specific activity was approximately 6000 dpm/µg of HSA in the diluted plasma.

Adsorption experiments were conducted identically for both the buffer and PPP solutions containing $^3$H-HSA. Circular disks (1 cm) of the surface-modified PE and PVC were placed in 20 ml scintillation vials; uncoated disks of the same materials were used as controls. The pieces were hydrated in 2 ml of TN overnight at room temperature. On the day of the experiment, $^3$H-HSA solutions (buffer or PPP) were prepared as described above. The hydration buffer was aspirated from the polymer samples and 1.0 ml of the radiolabeled HSA solution was added to the vial. The vials were gently agitated on an orbital shaker for 2 hours at room temperature. The HSA solution was aspirated and 4 ml of TNT solution (50 mM Tris, 150 mM NaCl, 0.05% Tween20, pH 7.5) were added to each vial; the vials were shaken for 15 minutes at room temperature. The TNT wash step was repeated two times and the disks were transferred to clean, dry scintillation vials. Two ml of THF were added to each vial and the samples were strongly agitated on an orbital shaker overnight. To each vial, 10 ml of Hionic Fluor were added and thoroughly mixed by vortexing. The vials were counted using a liquid scintillation counter (Packard 1900 CA). The surface concentration of HSA was calculated from these data using the specific activity of the HSA adsorption solution and the surface area of the disks.

PE and PVC were modified with heterobifunctional and polymeric compounds using the same procedures as described in Example 28. The results of the binding of $^3$H-HSA out of TN buffer solution onto the modified and uncoated PE and PVC materials are shown in Table 3.

TABLE 3

Adsorption of HSA from TN buffer onto modified PE and PVC surfaces

| Surface | Surface concentration of HSA (µg/cm$^2$) | |
|---|---|---|
| | PE | PVC |
| Uncoated | 0.069 ± 0.001 | 0.066 ± 0.000 |
| Compound 32B | 0.068 ± 0.001 | 0.051 ± 0.001 |
| Compound 32C | 0.050 ± 0.001 | 0.036 ± 0.001 |
| Compound 33B | 0.071 ± 0.002 | 0.066 ± 0.001 |
| Compound 33C | 0.054 ± 0.000 | 0.045 ± 0.006 |
| Compound 33D | 0.136 ± 0.000 | 0.036 ± 0.005 |
| Compounds 18, 19 | 0.128 ± 0.005 | 0.098 ± 0.006 |
| Compounds 10, 11 | 0.167 ± 0.006 | 0.168 ± 0.007 |
| Compounds 14, 15 | 0.191 ± 0.001 | 0.200 ± 0.010 |
| Compound 8, 9 | 0.191 ± 0.010 | 0.159 ± 0.007 |

The results of HSA binding from buffer solution indicated that many of the polymeric reagents bound HSA at similar levels to uncoated surfaces, whereas the heterobifunctional compounds enhanced binding by 2- to 3-fold over uncoated.

Example 31

HSA Binding from Plasma to PE Modified with Compounds 8, 9, 18, 19, 30, 32, and 33

PE flat substrates were modified with Compounds 8, 9, 18, 19, 30, 32, and 33. Compounds 8, 9, 18, 19, 32, and 33 were prepared in IPA at concentration of 1 mg/ml and Compound 30 was prepared in IPA/water (80/20 v/v), and substrates were coated following the procedure as described in Example 28. HSA binding from PPP was measured as described in Example 30; the specific activity was 2,003 dpm/µg.

TABLE 4

HSA binding from PPP onto PE

| Surface (PE) | Surface concentration (µg/cm$^2$) |
|---|---|
| Uncoated | 0.008 ± 0.001 |
| Compound 32B | 0.064 ± 0.012 |
| Compound 33A | 0.010 ± 0.000 |
| Compound 33B | 0.168 ± 0.002 |
| Compound 30 | 0.015 ± 0.000 |
| Compounds 18, 19 | 0.017 ± 0.002 |
| Compounds 8, 9 | 0.012 ± 0.001 |

Example 32

HSA Binding from Plasma to PVC Modified with Compounds 8, 9, 32, and 33

PVC flat substrates were modified with Compounds 8, 9, 32, and 33. The compounds were prepared in IPA at concentration of 1 mg/ml, and were applied to the substrates following the procedure as described in Example 28. HSA binding from PPP was measured as described in Example 30; in this experiment the specific activity was 3,150 dpm/µg HSA.

TABLE 5

HSA binding from PPP onto PVC

| Surface | Surface concentration (µg/cm$^2$) |
|---|---|
| Uncoated | 0.0183 ± 0.0005 |
| Compound 32C | 0.0460 ± 0.0040 |
| Compound 32B | 0.0420 ± 0.0010 |
| Compound 33C | 0.1720 ± 0.0120 |
| Compound 33B | 0.0830 ± 0.0020 |
| Compounds 8, 9 | 0.0296 ± 0.0010 |

Example 33

HSA Binding from Plasma to PE Modified with Compounds 14, 15

PE flat substrates were modified with Compounds 14, 15. The compounds were prepared in IPA at concentrations ranging from 1–10 mg/ml and applied as one coat or three coats, otherwise following the procedure as described in Example 28. HSA binding from PPP was measured as described in Example 30; specific activity of HSA was 5,636 dpm/µg in experiment #1 and #2. The results are shown in Table 6.

TABLE 6

HSA binding from PPP onto PE modified with Compounds 14, 15

| | Surface concentration of HSA (µg/cm$^2$) | |
|---|---|---|
| Surface | Experiment #1 | Experiment #2 |
| Uncoated PE | 0.14 ± 0.004 | 0.12 ± 0.005 |
| 1 mg/ml (3 coats) | 0.16 ± 0.008 | n.d.* |
| 2.5 mg/ml (3 coats) | 0.28 ± 0.011 | n.d. |
| 5 mg/ml (1 coat) | n.d. | 0.48 ± 0.014 |
| 5 mg/ml (3 coats) | 0.48 ± 0.016 | 1.22 ± 0.046 |
| 7.5 mg/ml (1 coat) | n.d. | 0.67 ± 0.024 |

TABLE 6-continued

HSA binding from PPP onto PE modified with Compounds 14, 15

| | Surface concentration of HSA ($\mu g/cm^2$) | |
|---|---|---|
| Surface | Experiment #1 | Experiment #2 |
| 7.5 mg/ml (3 coats) | 0.91 ± 0.018 | 1.02 ± 0.053 |
| 10 mg/ml (1 coat) | n.d. | 0.52 ± 0.012 |
| 10 mg/ml (3 coats) | 0.70 ± 0.037 | 1.18 ± 0.111 |

*n.d. is not determined

The results of this experiment indicate that increasing the concentration of applied reagent yields surfaces which show increased binding of HSA from PPP. In addition, increasing the number of coats of reagent applied to the surface yields increased binding of HSA from PPP.

Example 34

HSA Binding from Plasma to PE Modified with Compounds 10, 11

PE flat substrates were modified with Compounds 10, 11. The compounds were prepared in IPA at concentrations ranging from 1–15 mg/ml and applied in three coats, otherwise following the procedure as described in Example 28. HSA binding from PPP was measured as described in Example 30; specific activity of the HSA in plasma was 5,977 dpm/$\mu$g in Experiment #1 and 6,636 dpm/$\mu$g in Experiment #2.

TABLE 7

HSA binding from PPP onto PE modified with Compounds 10, 11

| | Surface concentration of HSA ($\mu g/cm^2$) | |
|---|---|---|
| Surface | Experiment #1 | Experiment #2 |
| Uncoated PE | 0.19 ± 0.024 | 0.22 ± 0.017 |
| 1 mg/ml | 0.43 ± 0.026 | n.d. |
| 2.5 mg/ml | 0.25 ± 0.016 | n.d. |
| 5 mg/ml | 0.64 ± 0.030 | n.d. |
| 7.5 mg/ml | 0.76 ± 0.084 | n.d. |
| 10 mg/ml | 1.04 ± 0.076 | 1.26 ± 0.092 |
| 12.5 mg/ml | n.d. | 0.91 ± 0.047 |
| 15 mg/ml | n.d. | 1.02 ± 0.052 |

The results of this experiment indicate that increasing the concentration of applied reagent yields increased HSA binding, although it appears as though the HSA binding reaches a plateau where further increases in the reagent applied to the surface provide no additional benefit. This may indicate that the surface has become saturated with reagent.

Example 35

HSA Binding to PE Modified with Compounds 8, 9

PE flat substrates were modified with Compounds 8, 9. The compounds were prepared in IPA at concentrations ranging from 1–10 mg/ml and applied as one coat or three coats, otherwise following the procedure as described in Example 28. HSA binding from PPP was measured as described in Example 30; specific activity in plasma was 6,045 dpm/$\mu$g HSA.

TABLE 8

HSA binding from PPP onto PE modified with Compounds 8, 9

| | Surface concentration of HSA ($\mu g/cm^2$) | |
|---|---|---|
| Surface | One coat | Three coats |
| Uncoated PE | 0.196 ± 0.034 | n.a. |
| 1 mg/ml | 0.194 ± 0.021 | 0.309 ± 0.039 |
| 2.5 mg/ml | 0.3403 ± 0.034 | 0.642 ± 0.069 |
| 5 mg/ml | 0.627 ± 0.067 | 0.692 ± 0.024 |
| 7.5 mg/ml | 1.043 ± 0.083 | 0.873 ± 0.063 |
| 10 mg/ml | 1.071 ± 0.197 | 1.067 ± 0.013 |

These coatings on PE and PVC enhanced HSA binding from buffer and plasma by as much as 10-fold. With some reagents (10, 11, 14, 15, and 8, 9), increasing concentration of coating solution produced surfaces with increasing capacity to bind HSA. This plateau occurred near 7.5 mg/ml for reagent 14, 15. For Compounds 8, 9, 10, 11, this plateau occurred near 10 mg/ml.

Example 36

Fibrinogen (Fgn) Adsorption from PPP onto Modified Substrates

PE and PVC substrates were modified with Compounds 8, 9, 18, 19, 32, and 33. The compounds were prepared in IPA at a concentration of 1.0 mg/ml and applied as a single coat, otherwise following the procedure as described in Example 28.

Adsorption of Fgn from human plasma (PPP) onto the control and surface-modified materials was quantified by using $^3$H-Fgn. Fgn was radiolabeled with $^3$H using sodium borohydride techniques (Means and Feeney, *Biochemistry* 7, 2192 (1968)) and stored frozen at 80° C. until used. Plasma solutions of Fgn for adsorption experiments were prepared using PPP (George King Biomedical; Overland Park, Kans.). On the day of the adsorption experiment, PPP was diluted 4:1 with TN buffer. The diluted PPP was then spiked with an aliquot of the stock $^3$H-Fgn solution to give a working solution with specific activity 1,816 dpm/$\mu$g Fgn.

Polymer samples (1 cm circular disks) were placed in 20 ml scintillation vials and hydrated overnight in 2.0 ml of TN at room temperature prior to protein adsorption. On the day of the experiment, the buffer solution was aspirated and 1.0 ml of the diluted PPP containing the $^3$H-Fgn was added to completely cover the polymer sample. The substrates were incubated in the $^3$H-Fgn solution for 2 hours at 23° C. The PPP solution was aspirated and the substrates washed three times with TNT (15 minutes each time). Disks were placed in clean scintillation vials, dissolved with THF, and counted for radioactivity as described in Example 30 for the HSA adsorption experiments. Surface concentrations of Fgn were calculated using the specific activity of the Fgn in the solution and the surface area of the polymer samples. The experimental results of the fibrinogen absorption experiments are shown in Table 10.

TABLE 10

Fgn adsorption to PE and PVC modified with
Compounds 8, 9, 18, 19, 32, and 33

| Surface treatment | Surface concentration of Fgn ($\mu g/cm^2$) | |
|---|---|---|
| | PE | PVC |
| Uncoated | 0.231 ± 0.152 | 0.269 ± 0.060 |
| Compound 33C | 0.148 ± 0.044 | 0.092 ± 0.003 |
| Compound 33B | 0.160 ± 0.013 | 0.112 ± 0.013 |
| Compound 32C | 0.129 ± 0.016 | 0.180 ± 0.005 |
| Compound 32B | 0.167 ± 0.016 | 0.249 ± 0.018 |
| Compounds 18, 19 | 0.131 ± 0.051 | 0.193 ± 0.029 |
| Compounds 8, 9 | 0.194 ± 0.032 | 0.222 ± 0.062 |

With these reagents, Fgn binding to modified surfaces was equal to or less than adsorption to uncoated surfaces. It is possible that the enhanced binding of HSA was responsible for reduced binding of Fgn. Surfaces that reduce the binding of Fgn are generally less likely to induce subsequent unfavorable responses from blood, such as fibrin formation and platelet adhesion.

Example 37

Binding of Anti-HSA Antibodies to Modified PE Exposed to HSA

PE substrates were modified with Compounds 8, 9, 18, 19, 30, 31, 32, and 33. The compounds were prepared in IPA at a concentration of 1.0 mg/ml and applied as a single coat, otherwise following the procedure as described in Example 28.

The binding of polyclonal anti-HSA antibodies was conducted using an ELISA technique to determine whether bound albumin maintained native structure in the absorbed state. Sheep anti-(HSA) antibodies conjugated to horseradish peroxidase (HRP) were obtained from Biodesign (Kennebunk, Me.). Polymer samples were hydrated with TN for 2 hours, and the protein solution was prepared with an HSA concentration of 1.0 mg/ml in TN. 1 ml of the protein solution was added to the samples and incubated for 2 hours at room temperature. After the adsorption, the solution was aspirated and the samples rinsed with TNT buffer. 1 ml of 1% BSA was added as a blocking step and incubated for one hour. The samples were washed twice with TNT for 30 min. each. After the wash, the samples were briefly rinsed with TN and incubated with the sheep-Ab-HRP in TN (diluted 1:2000), at room temperature for 1 hour with gentle agitation. The samples were washed 4 times with 3 mls TNT per vial by vortex. The pieces were transferred to test tubes and 1 ml TMB/peroxide solution was added. The color was allowed to develop for 15 minutes. The absorbance of the solutions was read at 655 nm using a spectrophotometer. The absorbance is directly proportional to the surface concentration of HRP and, therefore, also proportional to the surface concentration of anti-HSA antibody bound to the substrate surfaces.

TABLE 11

Results of anti-albumin antibody binding to HSA exposed surface

| Surface | Bound Ab ($A_{655}$) |
|---|---|
| Uncoated | 0.134 ± 0.005 |
| Compound 32A | 0.354 ± 0.030 |
| Compound 32B | 0.335 ± 0.022 |
| Compound 32C | 0.338 ± 0.017 |
| Compound 33A | 0.311 ± 0.026 |
| Compound 33B | 0.385 ± 0.034 |
| Compound 33C | 0.352 ± 0.020 |
| Compound 30 | 0.332 ± 0.016 |
| Compound 31 | 0.289 ± 0.025 |
| Compounds 8, 9 | 0.456 ± 0.016 |
| Compounds 18, 19 | 0.488 ± 0.020 |

The results of anti-HSA antibody binding to HSA previously absorbed from buffer to the uncoated and surface-modified materials indicated that there was little difference among the reagents tested. All surfaces bound high concentrations of antibody, about 3 to 4-fold higher than uncoated surfaces.

Example 38

Platelet Attachment and Activation from Platelet Rich Plasma (PRP) on Modified PE and PVC The surface-modified materials were incubated with platelet rich plasma (PRP) and then examined with a scanning electron microscope (SEM) to determine the influence of surface chemistry on platelet attachment and activation. Blood was collected fresh from human volunteers into 3.8% sodium citrate using 9:1 ratio of blood to anticoagulant. The blood was centrifuged at 1200 rpm for 15 min. to separate PRP from blood. The PRP was collected and kept at room temperature until used (less than 1 hour). The test samples (1 inch squares) were placed in a 6-well plate, 1 sample per well. To quantify the platelets in the plasma, a sample of the PRP was taken and diluted 1:100 with 1% ammonium oxalate. A capillary tube was used to transfer a small amount of solution to a hemacytometer, and the sample was incubated in a covered petri dish for 30 minutes for the platelets to settle. The platelets were counted under a phase contrast microscope and determined to be between $1.4$–$4.4 \times 10^{14}$ platelets/ml. The PRP solution was added onto the top of the samples until the entire surface was covered, and the samples were incubated one hour at room temperature with no agitation. After incubation, the PRP was removed carefully by aspiration and 3 mls of Tyrode's buffer (138 mM NaCl, 2.9 mM KCl, 12 mM sodium bicarbonate, pH 7.4) was gently added to each well. The plates were agitated slightly on an orbital shaker for 15 min.; the solution was changed and the wash repeated. The wash solution was aspirated and 2.0 ml of Karnovsky's fixative (25 mls formaldehyde+5 mls 25% glutaraldehyde+20 mls of a solution of 23% $NaH_2PO_4$—$H_2O$+77% $NaHPO_4$ anhydrous) were added to each well. The plate was wrapped with parafilm and incubated overnight with slight agitation. The fixative was aspirated and the samples were washed three times each with pure water, 15 minutes for each wash. The samples were then dehydrated with an ethanol series of 25, 50, 75, and 100%, for 15 minutes each. The samples were kept at 4° C. in 100% ethanol until mounted (up to 4 days). Samples were mounted and coated with Pd/Au and observed using a JEOL 840 scanning electron microscope. Photos were taken of different areas on the sample surface at several magnifications to give a representative view of each sample. The platelets were counted and judged for degree of activation using morphological descriptions based on Goodman et al *Scanning Electron Microscopy*/1984/I, 279–290 (1984).

The SEM results for two representative platelet attachment experiments are shown in Tables 12 and 13. From the SEM photographs, surface densities of bound platelets were estimated. The lowest platelet densities were found on the Compound 33C polymer consistently on both substrates. The Compound 32C polymer also had low platelet densities consistently. The predominant platelet morphologies are summarized in Table 13. Platelets that were rounded or dendritic were interpreted to be less activated; whereas the platelets that were spreading or fully spread and showed substantial aggregation were interpreted to be more extensively activated. For PE, the uncoated substrate had the highest platelet densities as well as the most fully spread platelet morphology. For PVC, the uncoated surface was poor but not the worst surface.

TABLE 12

Platelet Densities on modified surfaces (platelets/cm$^2$ × 10$^{-6}$).

| Reagent | PE | PVC |
|---|---|---|
| Uncoated | 980 ± 50 | 650 ± 0 |
| Compound 32C | 420 ± 0 | 400 ± 30 |
| Compound 33C | 220 ± 5 | 200 ± 30 |
| Compounds 18, 19 | 900 ± 30 | 1000 ± 200 |
| Compounds 8, 9 | 400 ± 40 | 400 ± 0 |

TABLE 13

Morphology of platelets attached to modified surfaces.

| Surface | PE | PVC |
|---|---|---|
| Compound 32B | Few aggregates, platelets mostly round or dendritic | |
| Compound 32C | Some aggregates, platelets mostly round or dendritic | Few aggregates, platelets mostly round or dendritic |
| Compound 33C | Few aggregates, platelets mostly round or dendritic | No aggregates, platelets mostly round |
| Compound 33D | Few aggregates, platelets mostly round or dendritic | Some aggregates, platelets dendritic or spread dendritic |
| Compounds 18, 19 | Many aggregates, most platelets spread or fully spread | Many aggregates, most platelets spreading or fully spread |
| Compounds 8, 9 | Many aggregates, most platelets spread or fully spread | Few aggregates, most platelets are spreading |
| Uncoated | Many aggregates, most platelets are fully spread | Few aggregates, platelets are spread dendritic or fully spread |

The polymeric reagents performed the best at reducing platelet attachment and activation on both substrates. The heterobifunctional reagents 8 and 9 performed similarly to the polymeric reagent 32C. The heterobifunctional reagents 18 and 19 were similar to or worse than the uncoated surface, depending on the substrate.

Example 39

Acute Dog Jugular Vein Implants with Catheters Modified with Compounds 6, 7

Surfaces modified with Compounds 6, 7 were tested using an acute, dog, jugular vein implant model. Surface-modified and control samples were implanted for one hour in the external jugular veins of 15–25 kg mixed-breed dogs. Attachment of $^{111}$In-labeled, autologous platelets was monitored spatially and quantitatively in real time using gamma camera imaging.

In each experiment, the dog was anesthetized with pentobarbital and secured in a supine position. No anticoagulant was given to the animals prior to or during the experiments. Ninety ml of blood was drawn into citrate/dextrose (9:1 v/v) and the platelets were isolated and labeled with $^{111}$In-oxine. The labeled platelets were reinfused into the dog and allowed to circulate for 20 minutes. In quick succession, one rod modified with a fatty acid derivative and one uncoated control rod were implanted bilaterally in the left and right external jugular veins. By using an uncoated control rod in each experiment, any variability in the response of individual animals to the implanted materials was accounted for. Immediately after insertion of the rods, the neck region of the dog was monitored continuously for one hour with a Picker 4/15 digital gamma camera to follow in real time the attachment of platelets onto the rods. The gamma camera allowed both digital quantification and spatial resolution of the radioactive counts. The data collected with the camera was transferred to a dedicated microcomputer to calculate the relative platelet adhesion rates on the coated and control materials. After the one hour scan, the animal was heparinized systemically, to stop any additional thrombogenesis, and euthanized with an intravenous injection of KCl. Each jugular vein was exposed and opened longitudinally to reveal the rod in place in the vein. After the rods were photographed, they were removed and the thrombus was stripped, lyophilized and weighed.

TABLE 14

Comparison of platelet attachment on PU modified with Compounds 6, 7.

| Surface | Platelet attachment rate versus control |
|---|---|
| Uncoated PU | 1.00 ± 0.43 |
| Modified with Compounds 6, 7 | 0.39 ± 0.35 |

The coated PU surface performed significantly better than the uncoated surface, reducing platelet adhesion in this acute test of blood compatibility.

Example 40

Five-month Sheep Mitral Valve Implants Using Modified Silicone Rubber Heart Valves Silicone rubber (SR) heart valves are modified with reagents 14, 15. The reagent is prepared at 5 mg/ml in IPA and applied, using procedures as described in Example 28, in three coats to the surface of the SR portions of a polymeric, tri-leaflet valve. The valves are sterilized using ethylene oxide and implanted in the mitral position in juvenile sheep using procedures described previously Irwin, E. D., et al, *J. Invest. Surg.* 6, 133–141 (1993). Three valves treated with the reagents are implanted. Valves are left in place for approximately 150 days. At the end of the implant period, the sheep are sacrificed and the hearts are explanted. The valve, including the surrounding heart tissue is removed and placed in buffered formalin. The valves are examined visually and photographed.

The appearance of the explanted valve leaflets should be improved by the coating. The coated valves should have minimal thrombus on the surface of the leaflets, whereas the uncoated SR valves should have substantial thrombus covering much of the surface of the leaflets. Furthermore, the thrombus present on the surface may be significantly mineralized, a further detrimental outcome that would potentially shorten the usable lifetime of the valve.

What is claimed is:

1. A method of preparing a passivating biomaterial surface, the method comprising the steps of coating a biomaterial surface with a reagent comprising a latent reactive group and a bifunctional aliphatic acid, both groups being covalently attached to a spacer in a manner that permits the latent reactive group to be activated in order to attach the reagent to the surface, and that permits the aliphatic acid of the attached reagent to attract and bind a proteinaceous moiety in order to passivate the surface and activating the latent reactive group(s) under conditions suitable to covalently bond the reagent to the surface.

2. A method according to claim 1 wherein the reagent comprises a divalent spacer in order to provide a heterobifunctional reagent.

3. A method according to claim 1 wherein the spacer comprises a polymeric backbone in order to provide a polymeric reagent.

4. A method according to claim 1 wherein the biomaterial is selected from the group consisting of polyolefins, polystyrenes, poly(methyl)methacrylates, polyacrylonitriles, poly(vinylacetates), poly (vinyl alcohols), poly(vinyl) chlorides, polyoxymethylenes, polycarbonates, polyamides, polyimides, polyurethanes, phenolics, amino-epoxy resins, polyesters, silicones, cellulose-based plastics, and rubber-like plastics.

5. A method according to claim 1 wherein the method comprises the step of coating a biomaterial surface with a reagent selected from the group consisting of mono-2-(carboxymethyl) hexadecanamidopoly (ethylene glycol)$_{200}$ mono-4-benzoylbenzyl ether, mono-3-carboxyheptadecanamidopoly (ethylene glycol)$_{200}$ mono-4-benzoylbenzyl ether, mono-2-(carboxymethyl) hexadecanamidotetra (ethylene glycol) mono-4-benzoylbenzyl ether, mono-3-carboxyhepta-decanamidotetra (ethylene glycol) mono-4-benzoylbenzyl ether, N-[2-(4-benzoylbenzyloxy) ethyl]-2-(carboxymethyl) hexadecanamide, N-[2-(4-benzoylbenzyloxy)ethyl]-3-carboxyheptadecanamide, N-[12-(benzoylbenzyloxy) dodecyl]-2-(carboxymethyl) hexadecanamide, N-[12-(benzoylbenzyloxy) dodecyl]-3-carboxy-heptadecanamide, N-[3-(4-benzoylbenzamido) propyl]-2-(carboxymethyl) hexadecanamide, N-[3-(4-benzoylbenzamido) propyl]-3-carboxyheptadecanamide, N-(3-benzoylphenyl)-2-(carboxymethyl) hexadecanamide, N-(3-benzoylphenyl)-3-carboxyheptadecanamide, N-(4-benzoylphenyl)-2-(carboxymethyl) hexadecanamide, poly (ethylene glycol)$_{200}$ mono-15-carboxypentadecyl mono-4-benzoylbenzyl ether, and mono-15-carboxypenta-decanamidopoly (ethylene glycol)$_{200}$ mono-4-benzoylbenzyl ether.

6. A method according to claim 5 wherein the biomaterial is selected from the group consisting of polyolefins, polystyrenes, poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, and cellulose-based plastics.

7. A passivating biomaterial prepared according to the method of claim 6.

8. A medical article fabricated from a passivating biomaterial according to claim 7.

9. A medical article according to claim 8, wherein the article comprises a blood-contacting medical device for in vivo application.

10. A medical article according to claim 9, wherein the article comprises a blood-contacting medical device for in vivo application.

* * * * *

UNITED STATES PATENT AND TRADEMARK OFFICE
Certificate

Patent No. 6,555,587 B1　　　　　　　　　　　　　　　　　　　　　　Patented: April 29, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Patrick E. Guire, Eden Prairie, MN (US); Aron B. Anderson, Minnetonka, MN (US); Richard A. Amos, St. Anthony, MN (US); Terrence P. Everson, Eagan, MN (US); and Peter Duquette, Edina, MN (US).

Signed and Sealed this Twentieth Day of February 2007.

WILLIAM R. DIXON, JR.
*Special Program Examiner*
Technology Center 1600

UNITED STATES PATENT AND TRADEMARK OFFICE
CERTIFICATE OF CORRECTION

PATENT NO.        : 6,555,587 B1                                Page 1 of 2
APPLICATION NO. : 10/207944
DATED             : April 29, 2003
INVENTOR(S)       : Guire et al.

It is certified that error appears in the above-identified patent and that said Letters Patent is hereby corrected as shown below:

Column 13, replace the notation for Compound/Example 11/8 with
-- N-[2-(4-Benzoylbenzyloxy)ethyl]-3-carboxyheptadecanamide--.

Column 15, replace the notation for Compound/Example 17/11 with
--N-(3-Benzoylphenyl)-3-carboxyhepta-decanamide--.

Column 16, replace the notation for Compound/Example 19/12 with
--N-(4-Benzoylphenyl)-3-carboxyhepta-decanamide--.

Column 17, replace the notation for Compound/Example 22/15 with -- Hexadecyl 4-benzoylbenzyl ether--.

Column 21, replace the formula for Compound/Example 30/22 with:
--

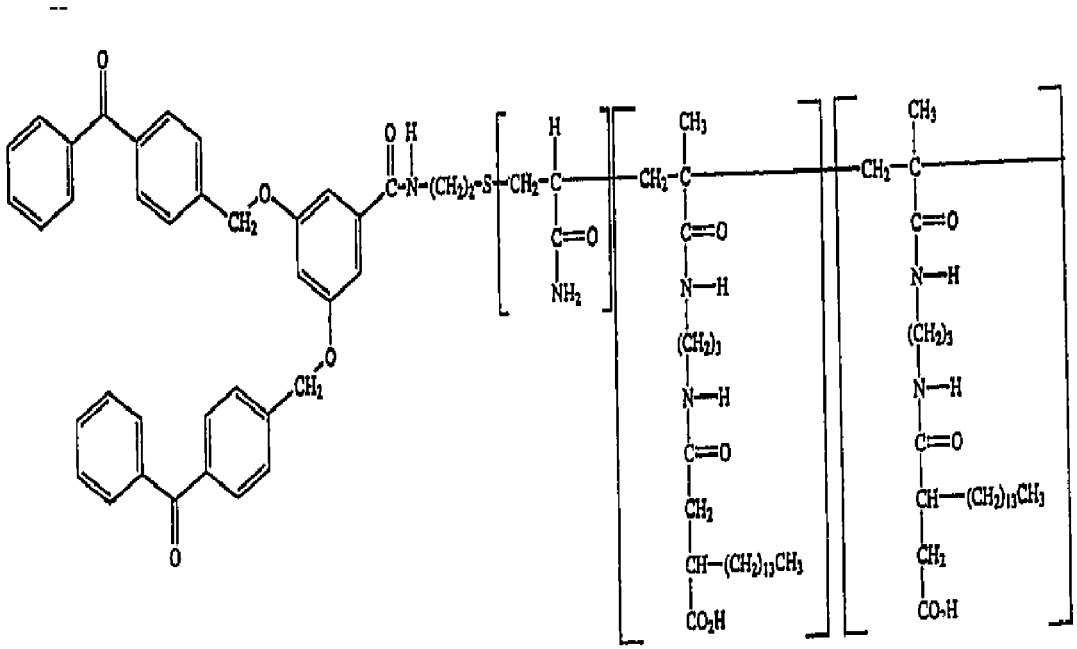

--

UNITED STATES PATENT AND TRADEMARK OFFICE
CERTIFICATE OF CORRECTION

PATENT NO.        : 6,555,587 B1
APPLICATION NO. : 10/207944
DATED             : April 29, 2003
INVENTOR(S)       : Guire et al.

It is certified that error appears in the above-identified patent and that said Letters Patent is hereby corrected as shown below:

Column 23, replace the formula for Compound/Example 32A-C/24 with:
--

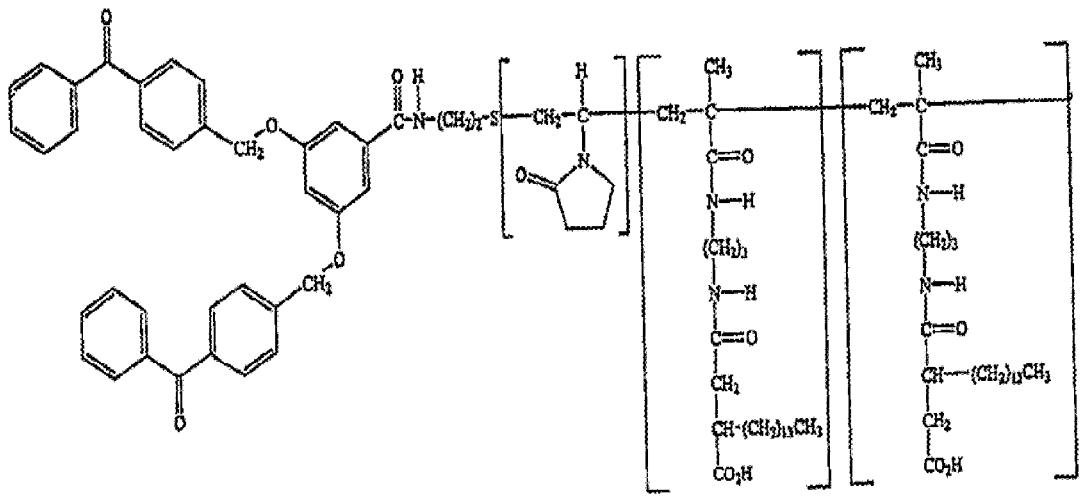

--

Signed and Sealed this

Seventh Day of August, 2007

JON W. DUDAS
*Director of the United States Patent and Trademark Office*